(12) United States Patent
Jourdan et al.

(10) Patent No.: US 6,635,262 B2
(45) Date of Patent: Oct. 21, 2003

(54) ROLL-ON APPLICATOR COMPRISING A HAIR COMPOSITION

(75) Inventors: Hervé Jourdan, Saint-Cyr (FR); Dorothée Pasquet, Bois Colombes (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/805,060

(22) Filed: Mar. 14, 2001

(65) Prior Publication Data

US 2003/0012758 A1 Jan. 16, 2003

(30) Foreign Application Priority Data

Mar. 14, 2000 (FR) .............................. 00 03251

(51) Int. Cl.[7] .............................. A61K 9/00; A61K 7/11; A61K 7/075
(52) U.S. Cl. .................. 424/400; 424/78.03; 424/70.1; 424/70.11; 424/70.12; 424/70.122; 424/70.16; 424/70.21; 424/70.22; 424/70.27; 424/70.31
(58) Field of Search .............................. 424/400, 78.03, 424/70.1, 70.11, 70.12, 70.122, 70.16, 70.21, 70.22, 70.27, 70.31

(56) References Cited

U.S. PATENT DOCUMENTS

| | | |
|---|---|---|
| 2,047,398 A | 7/1936 | Voss et al. |
| 2,261,002 A | 10/1941 | Ritter |
| 2,271,378 A | 1/1942 | Searle |
| 2,273,780 A | 2/1942 | Dittmar |
| 2,375,853 A | 5/1945 | Kirby et al. |

(List continued on next page.)

FOREIGN PATENT DOCUMENTS

| | | |
|---|---|---|
| DE | 44 02 929 | 6/1995 |
| DE | 44 20 736 | 8/1995 |
| DE | 44 24 530 | 1/1996 |
| DE | 44 24 533 | 1/1996 |
| EP | 0 080 976 | 6/1983 |

(List continued on next page.)

OTHER PUBLICATIONS

Charles Todd et al., "Volatile Silicone Fluids for Cosmetic Formulations", Cosmetics and Toiletries, vol. 91, Jan. 1976, pp. 29–32.
Patrick D. Dorgan, Waxes in Cosmetics, Drug & Cosmetic Industry, Dec. 1983, pp. 30–33.
English language Derwent Abstract of DE 44 02 929, Jun. 22, 1995.
English language Derwent Abstract of DE 44 20 736, Aug. 10, 1995.
English language Derwent Abstract of DE 44 24 530, Jan. 18, 1996.

(List continued on next page.)

*Primary Examiner*—Thurman K. Page
*Assistant Examiner*—Blessing Fubara
(74) *Attorney, Agent, or Firm*—Finnegan, Henderson, Farabow, Garrett & Dunner, L.L.P.

(57) ABSTRACT

A roll-on applicator comprising a container and a rotatable application member on the container, such as a container closed at one end by a closure means which can move in rotation, and means for retaining the closure means, the container containing a hair composition devoid of carboxylic surfactant, said hair composition comprising, in a cosmetically acceptable medium, at least one component chosen from:

(i) anionic, amphoteric, and nonionic fixing polymers;
(ii) beneficial agents; and
(iii) hair dyes;

wherein the roll-on applicator is capable of directly depositing on the hair said at least one component.

86 Claims, 1 Drawing Sheet

U.S. PATENT DOCUMENTS

| | | |
|---|---|---|
| 2,388,614 A | 11/1945 | Kirby et al. |
| 2,454,547 A | 11/1948 | Bock et al. |
| 2,723,248 A | 11/1955 | Wright |
| 2,798,053 A | 7/1957 | Brown |
| 2,923,692 A | 2/1960 | Ackerman et al. |
| 2,961,347 A | 11/1960 | Floyd |
| 3,036,328 A | 5/1962 | Schaich |
| 3,206,462 A | 9/1965 | McCarty |
| 3,227,615 A | 1/1966 | Korden |
| 3,576,592 A | 4/1971 | Zviak et al. |
| 3,632,559 A | 1/1972 | Matter et al. |
| 3,716,633 A | 2/1973 | Viout et al. |
| 3,836,537 A | 9/1974 | Boerwinkle et al. |
| 3,874,870 A | 4/1975 | Green et al. |
| 3,917,817 A | 11/1975 | Vanlerberghe et al. |
| 3,929,990 A | 12/1975 | Green et al. |
| 3,966,904 A | 6/1976 | Green et al. |
| 4,001,432 A | 1/1977 | Green et al. |
| 4,005,193 A | 1/1977 | Green et al. |
| 4,013,787 A | 3/1977 | Varlerberghe et al. |
| 4,025,617 A | 5/1977 | Green et al. |
| 4,025,627 A | 5/1977 | Green et al. |
| 4,025,653 A | 5/1977 | Green et al. |
| 4,026,945 A | 5/1977 | Green et al. |
| 4,027,008 A | 5/1977 | Sokol |
| 4,027,020 A | 5/1977 | Green et al. |
| 4,031,307 A | 6/1977 | DeMartino et al. |
| 4,070,533 A | 1/1978 | Papantoniou et al. |
| 4,076,912 A | 2/1978 | Papantoniou et al. |
| 4,128,631 A | 12/1978 | Lundmark et al. |
| 4,131,576 A | 12/1978 | Iovine et al. |
| 4,137,180 A | 1/1979 | Naik et al. |
| 4,137,208 A | 1/1979 | Elliott |
| 4,172,887 A | 10/1979 | Vanlerberghe et al. |
| 4,221,494 A | 9/1980 | Kachur |
| 4,221,495 A | 9/1980 | Braun et al. |
| 4,223,009 A | 9/1980 | Chakrabarti |
| 4,237,243 A | 12/1980 | Quack et al. |
| 4,277,581 A | 7/1981 | Vanlerberghe et al. |
| 4,282,203 A | 8/1981 | Jacquet et al. |
| 4,349,532 A | 9/1982 | Vanlerberghe et al. |
| 4,475,837 A | 10/1984 | Dornbusch et al. |
| 4,591,610 A | 5/1986 | Grollier |
| 4,608,250 A | 8/1986 | Jacquet et al. |
| 4,693,935 A | 9/1987 | Mazurek |
| 4,719,099 A | 1/1988 | Grollier et al. |
| 4,728,571 A | 3/1988 | Clemens et al. |
| 4,761,273 A | 8/1988 | Grollier et al. |
| 4,839,166 A | 6/1989 | Grollier et al. |
| 4,874,554 A | 10/1989 | Lange et al. |
| 4,957,732 A | 9/1990 | Grollier et al. |
| 4,972,037 A | 11/1990 | Garbe et al. |
| 4,996,059 A | 2/1991 | Grollier et al. |
| 5,051,017 A | 9/1991 | Yorks |
| 5,139,037 A | 8/1992 | Grollier et al. |
| 5,196,189 A | 3/1993 | Jacquet et al. |
| 5,690,924 A * | 11/1997 | Keil et al. ............... 424/78.03 |
| 5,773,611 A | 6/1998 | Zysman et al. |
| 5,914,103 A | 6/1999 | Armbruster et al. |
| 5,937,866 A | 8/1999 | Magharehi |

FOREIGN PATENT DOCUMENTS

| | | |
|---|---|---|
| EP | 0 122 324 | 10/1984 |
| EP | 0 227 994 | 7/1987 |
| EP | 0 337 354 | 10/1989 |
| EP | 0 412 704 | 2/1991 |
| EP | 0 412 707 | 2/1991 |
| EP | 0 486 135 | 5/1992 |
| EP | 0 582 152 | 2/1994 |
| EP | 0 646 572 | 4/1995 |
| FR | 1 222 944 | 6/1960 |
| FR | 1 400 366 | 4/1965 |
| FR | 1 492 597 | 8/1967 |
| FR | 1 564 110 | 4/1969 |
| FR | 1 580 545 | 9/1969 |
| FR | 1 583 363 | 10/1969 |
| FR | 2 077 143 | 10/1971 |
| FR | 2 080 759 | 11/1971 |
| FR | 2 162 025 | 7/1973 |
| FR | 2 190 406 | 2/1974 |
| FR | 2 252 840 | 6/1975 |
| FR | 2 265 781 | 10/1975 |
| FR | 2 265 782 | 10/1975 |
| FR | 2 270 846 | 12/1975 |
| FR | 2 280 361 | 2/1976 |
| FR | 2 316 271 | 1/1977 |
| FR | 2 320 330 | 3/1977 |
| FR | 2 336 434 | 7/1977 |
| FR | 2 350 384 | 12/1977 |
| FR | 2 357 241 | 2/1978 |
| FR | 2 368 508 | 5/1978 |
| FR | 2 383 660 | 10/1978 |
| FR | 2 393 573 | 1/1979 |
| FR | 2 413 907 | 8/1979 |
| FR | 2 416 723 | 9/1979 |
| FR | 2 439 798 | 5/1980 |
| FR | 2 470 596 | 6/1981 |
| FR | 2 505 348 | 11/1982 |
| FR | 2 519 863 | 7/1983 |
| FR | 2 542 997 | 9/1984 |
| FR | 2 589 476 | 5/1987 |
| FR | 2 598 611 | 11/1987 |
| FR | 2 673 179 | 8/1992 |
| GB | 839 805 | 6/1960 |
| WO | WO 93/23009 | 11/1993 |
| WO | WO 93/23446 | 11/1993 |
| WO | WO 94/07844 | 4/1994 |
| WO | WO 94/10131 | 5/1994 |
| WO | WO 94/24097 | 10/1994 |
| WO | WO 95/00578 | 1/1995 |
| WO | WO 95 05154 | 2/1995 |
| WO | WO 95/16665 | 6/1995 |
| WO | WO 95/23807 | 9/1995 |

OTHER PUBLICATIONS

English language Derwent Abstract of DE 44 24 533, Jan. 18, 1996.

English language Derwent Abstract of EP 0 080 976, Jun. 8, 1983.

English language Derwent Abstract of FR 1 565 110, Mar. 10, 1969.

English language Derwent Abstract of FR 2 077 143, Oct. 15, 1971.

English language Derwent Abstract of FR 2 080 759, Nov. 19, 1971.

English language Derwent Abstract of FR 2 320 330, Mar. 4, 1977.

English language Derwent Abstract of FR 2 336 434, Jul. 22, 1977.

English language Derwent Abstract of FR 2 589 476, May 7, 1987.

ROLL-ON APPLICATOR COMPRISING A HAIR COMPOSITION

The invention relates to a roll-on applicator comprising a hair composition. The invention also relates to a hair cosmetic process comprising the use of this applicator.

Hair compositions which are provided in various forms, such as creams, lotions, bottles, tubes, sticks, solutions to be applied using a pad, or aerosols, are known.

Each form of presentation may exhibit disadvantages. For example, when the composition is provided in the foam of a cream, lotion, bottle or tube, the user may have to take the composition between the fingers and deposit it on the hair. In this case, it may be necessary to wash or wipe the hands after the application of the hair product in order to prevent the hands from becoming sticky, tacky, or greasy, which may render the use of such products inconvenient.

When the composition is composed in the form of a stick or is applied from a pad, a possible disadvantage is that hairs may remain stuck to the stick or the pad, which may present hygienic and aesthetic problems. It may be, therefore, displeasing to envisage the use of the same stick or the same pad applicator by several people.

When the composition is applied in the form of an aerosol, it is typically distributed from an aerosol container via a valve by the action of a propellant. In this case, the diffused product may not be localized with accuracy lock by lock.

Roll-on applicators, for example those disclosed in Patents U.S. Pat. No. 3,036,328, U.S. Pat. No. 4,221,494, U.S. Pat. No. 4,221,495, U.S. Pat. No. 4,475,837 and U.S. Pat. No. 5,051,017, the disclosures of which are incorporated herein by reference, are also known. Provision has been made for the use of such roll-on applicators in cosmetics, such as for the application of skin hygiene products.

Thus, one subject of the present invention is a device including a hair composition for the form retention of the hairstyle and the care of the hair, which can give rise to at least one of convenient and hygienic application.

It has been found that by appropriately selecting the constituents of the hair composition, on the one hand, and certain applicational parameters for these compositions by a careful choice of a roll-on applicator, on the other hand, it is possible to address at least one ("at least one" is used throughout in its normal sense, to denote one or more) of the problems listed above.

As used herein, the term "copolymers of A and B" means copolymers formed from monomers comprising A and B. For example, "copolymers of vinyl acetate and of acrylic ester" are copolymers formed from monomers comprising vinyl acetate and acrylic ester.

As used herein, the term "a hair composition devoid of carboxylic surfactant" means a hair composition containing no surfactant having any —COOH functionality.

As used herein, unless expressly specified otherwise, the term "lower alkyl" means a $C_1$–$C_6$ alkyl group.

A subject of the invention is a roll-on applicator comprising a container and a rotatable application member on the container, the container containing a hair composition devoid of carboxylic surfactant, said hair composition comprising, in a cosmetically acceptable medium, at least one component chosen from:

(i) anionic, amphoteric, and nonionic fixing polymers;
(ii) beneficial agents; and
(iii) hair dyes;

wherein the roll-on applicator is capable of directly depositing on the hair said at least one component.

For example, the roll on applicator can be closed at one end by a closure means which can move in rotation, and can contain means for retaining the closure means.

For example, the roll-on applicator can be used for directly depositing on the hair at least one product chosen from styling and care products. Such products can include, for example, hairstyle products, fixing products, and products providing at least one beneficial effect on the cosmetic condition of the hair or sheen.

Another subject-matter of the present invention is a cosmetic process comprising the use of the roll-on applicator to apply said at least one component to the hair.

The accompanying drawings are included to provide a further understanding of the invention and are incorporated in and constitute a part of this specification. The drawings illustrate various aspects of an embodiment of the applicator according to the invention and, together with the description, serve to explain principles of the invention.

BRIEF DESCRIPTION OF THE DRAWINGS

In the drawings,

FIG. 1 shows an example of a roll-on applicator 10 comprising a container 12 and a rotatable application member 14 on the container 12. The container 12 contains a hair composition according to the present invention.

The application member 14 may close an open end of the container 12. The application member 14 may be in flow communication with the hair composition contained in the container 12. The application member can have any shape, for example a spherical, oval, regular, or irregular shape having a smooth or nonsmooth surface. The applicaton member 14 may be retained on the container 12 so that the application member 14 is rotatably movable. For example, a retainer 16 may be provided to retain the application member 14 on the container 12 while permitting the rotation of the application member 14 during product application.

An example of a roll-on applicator which may be used in the invention is the roll-on applicator sold by Weener Plastic under the designation "ball and ball carrier assembly for roll-on" (Narta type).

Figure 1:
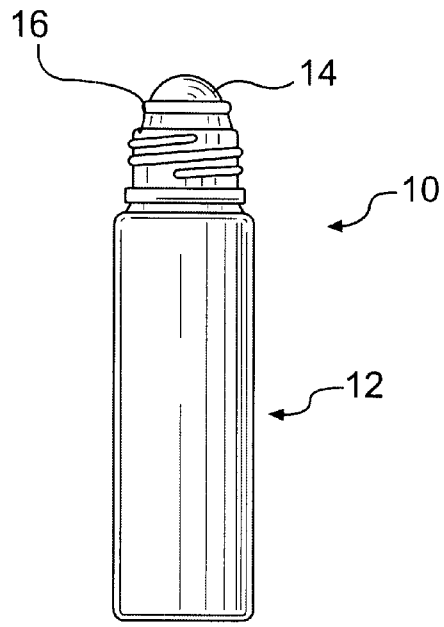
FIG. 1 is a side view of an embodiment of a roll-on applicator according to the present invention.
Figure 2:
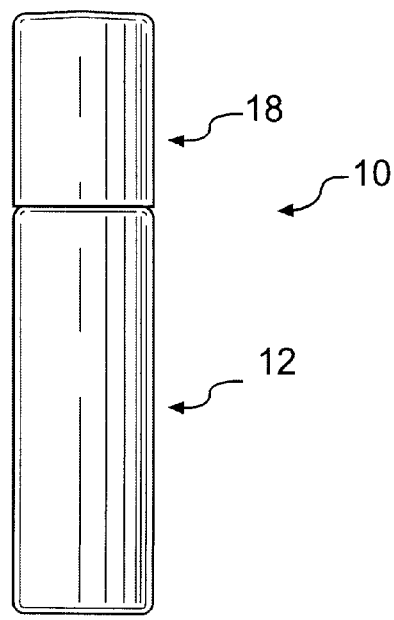
FIG. 2 is a side view of the applicator of FIG. 1 with a cap engaged on the applicator to cover an application member of the applicator.

As shown in FIG. 2, the applicator 10 optionally has a removable cap 18 configured to cover the application member 14. The cap 18 may be releasably engaged with the container 12 in any known manner. For example, the cap 18 and the container 12 may have cooperating screw threading.

According to the present invention, the term "beneficial effect on the cosmetic condition of the hair" is understood to mean any cosmetic improvement in the quality of the hair or in its appearance, such as, for example, an improvement in the ease of disentangling of the hair, an improvement in the softness to the touch of the hair, an improvement in the smoothing of the hair, and an improvement in the visual appearance of the hair, such as its coloring.

The term "hair composition" is understood to mean any composition useful for maintaining the hair, such as, for example, retaining the form the hairstyle, fixing the hairstyle, caring for the hair, making up the hair, and coloring the hair.

The word "styling" is understood to include the effect of fixing the form of the hairstyle. The word "styling" is also understood to include the effect of retaining the form of the hairstyle.

The word "care" is understood to include the effect of improving at least one property of the hair. The word "care" is also understood to include the effect of retaining at least one property of the hair. These properties may include, for example, the natural, cosmetic, and mechanical properties of the hair.

The term "fixing polymer" is understood to include polymers capable of fixing the form of the hairstyle. The term "fixing polymer" is also understood to include polymers capable of retaining the form of the hairstyle.

At least one fixing polymer may be used in the dissolved form. At least one fixing polymer may also be in the form of a dispersion of solid polymer particles.

The at least one fixing polymer may be selected from anionic, amphoteric, and nonionic fixing polymers. Anionic, amphoteric, and nonionic fixing polymers that may be used according to the invention are described below.

The anionic fixing polymers include polymers comprising at least one group derived from carboxylic, sulfonic, and phosphoric acid having a molecular weight generally ranging for example from approximately 500 to 5,000,000.

The anionic fixing polymers include, for example

1) Polymers comprising at least one carboxyl repeating unit derived from unsaturated mono- and dicarboxylic acid monomers of formula:

wherein:
n is an integer ranging from 0 to 10;
$A_1$ is a methylene group, optionally connected to the carbon atom of the unsaturated group and, in addition, optionally connected to a neighboring methylene group when n is greater than 1 via a heteroatom, such as a heteroatom chosen from oxygen and sulfur;
$R_7$ is chosen from hydrogen atoms, phenyl groups, and benzyl groups;
$R_8$ is chosen from hydrogen atoms, lower alkyl groups, and carboxyl groups; and
$R_9$ is chosen from hydrogen atoms, lower alkyl groups, —$CH_2$—COOH groups, phenyl groups, and benzyl groups.

In the abovementioned formula, a lower alkyl group can denote a group comprising 1 to 4 carbon atoms, for example, methyl groups and ethyl groups.

Non-limiting examples of anionic fixing polymers comprising carboxyl groups according to the invention include:

A) Homo- and copolymers of acrylic and methacrylic acid and homo- and copolymers of acrylic and methacrylic acid salts such as, for example, the products sold under the names Versicol E and K by Allied Colloid and Ultrahold by BASF. The copolymers of acrylic acid and of acrylamide sold in the form of their sodium salt under the names Reten 421, 423 and 425 by Hercules, and the sodium salts of polyhydroxycarboxylic acids.

B) Copolymers of acrylic acid and methacrylic acid with at least one monoethylenic unit, such as ethylene, styrene, vinyl esters and esters of acrylic and methacrylic acid, optionally grafted onto a polyalkylene glycol, such as polyethylene glycol, and optionally crosslinked. Such polymers are disclosed, for example, in French Patent 1,222,944 and German Application 2,330,956, the disclosures of which are incorporated herein by reference; the copolymers of this type comprising, in their chain, at least one optionally linked unit chosen from N-alkylated and -hydroxyalkylated acrylamide units, such as disclosed, for example, in Luxembourgian Patent Applications 75370 and 75371, the disclosures of which are incorporated herein by reference, and provided under the name Quadramer by American Cyanamid. Mention may also be made of copolymers of acrylic acid and of $C_1$–$C_4$ alkyl methacrylate and terpolymers of vinylpyrrolidone, of acrylic acid and of $C_1$–$C_{20}$ alkyl methacrylate, for example lauryl methacrylate, such as that sold by ISP under the name Acrylidone LM, and methacrylic acid/ethyl acrylate/tert-butyl acrylate terpolymers, such as the product sold under the name Luvimer 100 P by BASF.

C) Copolymers derived from crotonic acid, such as those comprising, in their chain, at least one unit chosen from vinyl acetate and propionate units and optionally other units, such as allyl and methallyl esters, vinyl ethers and vinyl esters of linear and branched saturated carboxylic acids comprising a long hydrocarbon-based chain, such as those comprising at least 5 carbon atoms, wherein it is optionally possible for these polymers to be grafted and crosslinked; and alternatively vinyl, allyl, and methallyl esters of α- and β-cyclic carboxylic acids. Such polymers, for example, are disclosed, inter alia, in French Patents 1,222,944, 1,580,545, 2,265, 782, 2,265,781, 1,564,110 and 2,439,798, the disclosures of which are incorporated herein by reference. Commercial products coming within this class are the Resins 28-29-30, 26-13-14 and 28-13-10 sold by National Starch, EX-SDR26, sold by B. F. Goodrich, and Aristoflex A, sold by Clariant. Aristoflex A is a member of a class called VA/crotonates copolymer, the class being defined as a copolymer of vinyl acetate and one or more monomers chosen from crotonic acid its simple esters. See International Cosmetic Ingredient Dictionary and Handbook, Seventh Edition, 1997, Volume 2, page 1451, the disclosure of which is incorporated by reference herein.

D) Copolymers derived from $C_4$–$C_8$ monounsaturated carboxylic acids and anhydrides chosen from:
copolymers comprising (i) at least one unit chosen from maleic, fumaric, and itaconic acids and anhydrides, and (ii) at least one unit chosen from vinyl esters, vinyl ethers, vinyl halides, phenylvinyl derivatives, acrylic acids and acrylic acid esters; the anhydride functional groups of these copolymers optionally being monoesterified and monoamidated; such polymers are disclosed, for example, in Patents U.S. Pat. Nos. 2,047,398, 2,723,248 and 2,102,113 and Patent GB, 839,805, the disclosures of which are incorporated herein by reference, and, for example, those sold under the names Gantrez AN and ES by ISP.
copolymers comprising (i) at least one unit chosen from maleic, citraconic, and itaconic anhydrides, and (ii) at least one unit chosen from allyl and methallyl esters, optionally comprising at least one unit chosen from acrylamide, methacrylamide, α-olefins, acrylic esters, methacrylic esters, acrylic acids, methacrylic acids, and vinylpyrrolidone groups,
the anhydride functional groups of these copolymers optionally being monoesterified and monoamidated.

These polymers are, for example, disclosed in French Patents 2,350,384 and 2,357,241 of L'Oréal, the disclosures of which are incorporated herein by reference.

E) Polyacrylamides comprising carboxylate groups.

The polymers comprising sulfo groups may comprise at least one unit chosen from vinylsulfonic, styrenesulfonic, naphthalenesulfonic, and acrylamidoalkylsulfonic units.

These polymers may, for example, be chosen from:
- salts of polyvinylsulfonic acid having a molecular weight generally ranging, for example, from approximately 1000 to 100,000, as well as copolymers with at least one unsaturated unit, such as, for example, acrylic and methacrylic acids and acrylic and methacrylic acid esters as well as acrylamide and its derivatives, vinyl ethers and vinylpyrrolidone.
- salts of polystyrenesulfonic acid, the sodium salts having, for example, a molecular weight of approximately 500,000 and of approximately 100,000 sold respectively under the names Flexan 500 and Flexan 130 by National Starch. These compounds are disclosed in Patent FR 2,198,719, the disclosure of which is incorporated herein by reference.
- salts of polyacrylamidosulfonic acids, such as, for example, those mentioned in Patent U.S. Pat. No. 4,128,631, the disclosure of which is incorporated herein by reference, and the polyacrylamidoethylpropanesulfonic acid sold under the name Cosmedia Polymer HSP 1180 by Henkel.

According to the invention, the anionic fixing polymers may, for example, be chosen from acrylic acid copolymers, such as the acrylic acid/ethyl acrylate/N-tert-butylacrylamide terpolymer sold under the name Ultrahold Strong by BASF; copolymers derived from crotonic acid, such as the vinyl acetate/vinyl tert-butylbenzoate/crotonic acid terpolymers and the crotonic acid/vinyl acetate/vinyl neododecanoate terpolymers sold under the name Resin 28-29-30 by National Starch; polymers derived from maleic, fumaric, and itaconic acids and anhydrides with vinyl esters, vinyl ethers, vinyl halides, phenylvinyl derivatives, and acrylic acid and its esters, such as the monoesterified methyl vinyl ether/maleic anhydride copolymer sold under the name Gantrez ES 425 by ISP; copolymers of methacrylic acid and of methyl methacrylate sold under the name Eudragit L by Rohm Pharma; the copolymer of methacrylic acid and of ethyl acrylate sold under the name Luvimer MAEX and MAE by BASF; the vinyl, acetate/crotonic acid copolymer sold under the name Luviset CA 66 by BASF; and the vinyl acetate/crotonic acid copolymer grafted by polyethylene glycol sold under the name Aristoflex A by Clariant.

Non-limiting examples of anionic fixing polymers include those chosen from the monoesterified methyl vinyl ether/maleic anhydride copolymer sold under the name Gantrez ES 425 by ISP; the acrylic acid/ethyl acrylate/N-tert-butylacrylamide terpolymer sold under the name Ultrahold Strong by BASF; the copolymers of methacrylic acid and of methyl methacrylate sold under the name Eudragit L by Rohm Pharma; the vinyl acetate/vinyl tert-butylbenzoate/crotonic acid terpolymers and the crotonic acid/vinyl acetate/vinyl neododecanoate terpolymers sold under the name Resin 28-29-30 by National Starch; the copolymer of methacrylic acid and of ethyl acrylate sold under the name Luvimer MAEX and MAE by BASF and the vinylpyrrolidone/acrylic acid/lauryl methacrylate terpolymer sold under the name Acrylidone LM by ISP.

The amphoteric fixing polymers which may be used in accordance with the invention may be chosen from polymers comprising B and C units distributed randomly in the polymer chain, where B denotes a unit deriving from a monomer comprising at least one basic nitrogen atom and C denotes a unit deriving from an acidic monomer comprising at least one group chosen from carboxyl and sulfo groups. Alternatively, B and C can denote groups deriving from monomers chosen from zwitterionic carboxybetaine and sulfobetaine monomers;

B and C may also denote a cationic polymer chain comprising at least one group selected from primary, secondary, tertiary and quaternary amine groups, in which at least one of the amine groups carries a group selected from carboxyl and sulfo groups connected via a hydrocarbon-based radical. Alternatively, B and C can form part of a chain of a polymer comprising at least one $\alpha,\beta$-dicarboxyethylene unit, at least one of the carboxyl groups of which has been reacted with a polyamine comprising at least one group selected from primary and secondary amine groups.

Non-limiting examples of amphoteric fixing polymers corresponding to the definition given above include:
(1) Polymers resulting from the copolymerization of a monomer derived from a vinyl compound substituted with at least one carboxylic group and of a basic monomer derived from a substituted vinyl compound comprising at least one basic atom.

Non-limiting examples of carboxylic groups used include carboxylic groups chosen from acrylic acid, methacrylic acid, maleic acid, and $\alpha$-chloroacrylic acid.

Non-limiting examples of basic monomers used include those chosen from dialkylaminoalkyl methacrylate, dialkylaminoalkyl acrylate, dialkylaminoalkylmethacrylamide and dialkylaminoalkylacrylamide.

Such compounds are described, for example, in U.S. Pat. No. 3,836,537, the disclosure of which is incorporated herein by reference.

(2) Polymers comprising at least one unit derived from:
a) at least one monomer chosen from acrylamides substituted on the nitrogen with an alkyl radical and methacrylamides substituted on the nitrogen with an alkyl radical,
b) at least one acidic comonomer comprising at least one reactive carboxylic group, and
c) at least one basic comonomer such as, for example, comonomers chosen from esters of acrylic acid and esters of methacrylic acid, said esters being substituted with at least one amine chosen from primary, secondary, tertiary, and quaternary amines, and products of quaternization of dimethylaminoethyl methacrylate with at least one sulfate chosen from dimethyl suplhate and diethyl sulfate.

Some embodiments according to the invention utilize N-substituted acrylamides and methacrylamides comprising $(C_2-C_{12})$alkyl groups such as N-ethylacrylamide, N-tert-butylacrylamide, N-tert-octylacrylamide, N-octylacrylamide, N-decylacrylamide, N-dodecylacrylamide as well as the corresponding methacrylamides.

Non-limiting examples of acidic comonomers include acidic comonomers chosen from acrylic acid, methacrylic acid, crotonic acid, itaconic acid, maleic acid and fumaric acid and $(C_1-C_4)$alkyl monoesters, chosen from maleic acid, fumaric acid, maleic anhydride and fumaric anhydride.

Non-limiting examples of basic comonomers include basic comonomers chosen from methacrylates of aminoethyl, butylaminoethyl, N,N'-dimethylaminoethyl and N-tert-butylaminoethyl.

Further non-limiting examples include copolymers having the CTFA (4th edition, 1991) name octylacrylamide/acrylates/butylaminoethyl methacrylate copolymer such as, for example, the products sold under the name Amphomer and Lovocryl 47 by the company National Starch.

(3) Amphoteric fixing polymers chosen from partially and completely crosslinked and alkylated polyamino amides partially derived from polyamino amides of formula:

$$\pm CO-R_{10}-CO-Z\pm \quad (II)$$

wherein:

$R_{10}$ is a divalent group derived from compounds chosen from: saturated dicarboxylic acids, dicarboxylic aromatic acids, carboxylic aliphatic acids chosen from monocarboxylic aliphatic acids and dicarboxylic aliphatic acids comprising at least one ethylenic double bond, and esters of $(C_1-C_6)$alkanols of said acids, and $R_{10}$ is also a divalent group derived from the addition of any one of the aforementioned acids with an amine chosen from bis(primary) and bis(secondary) amines, and Z is a divalent group derived from polyalkylene-polyamines chosen from bis(primary), mono- and bis(secondary) polyalkylene-polyamines. Non-limiting examples include:

a) in amounts generally ranging from 60 to 100 mol %, the group $$-NH-\pm(CH_2)_z-NH\pm_p- \quad (IV)$$

wherein x=2 and p=2 or 3, or alternatively x=3 and p=2 wherein group Z is derived from a compound chosen from diethylenetriamine, triethylenetetraamine, and dipropylenetriamine;

b) in an amount generally ranging from 0 to 40 mol %, (1) said groups (IV)' above wherein x=2 and p=1, and which said group is derived from at least one compound chosen from ethylenediamine, and (2) groups derived from piperazine:

—N⟨ ⟩N— c) in an amount generally ranging from 0 to 20 mol %, the group $-NH-(CH_2)_6-NH-$, derived from hexamethylenediamine, wherein these polyamino amines are crosslinked by adding at least one bifunctional crosslinking agent (chosen from epihalohydrins, diepoxides, dianhydrides and bis-unsaturated derivatives), present in an amount generally ranging from 0.025 to 0.35 mol of crosslinking agent per amine group of the polyamino amide and alkylated by the action of at least one compound chosen from acrylic acid, chloroacetic acid and alkane sultones, and salts of said alkane sultones.

The saturated dicarboxylic acids are for example chosen from saturated $(C_6-C_{10})$ dicarboxylic acids such as adipic, 2,2,4-trimethyladipic and 2,4,4-trimethyladipic acid. Representative dicarboxylic aromatic acids include for example $(C_6-C_{10})$ dicarboxylic aromatic acids, such as terephthalic acid. And representative mono- and dicarboxylic aliphatic acids comprising at least one ethylenic double bond include for example acrylic, methacrylic, and itaconic acids.

The alkane sultones used in the alkylation may optionally be chosen from propane sultone and butane sultone, and the salts of the alkylating agents can be chosen from sodium and potassium salts of said alkylating agents.

(4) Amphoteric fixing polymers comprising at least one zwitterionic unit of formula:

$$R_{11}\pm\overset{R_{12}}{\underset{R_{13}}{C}}\pm_y\overset{R_{14}}{\underset{R_{15}}{N^+}}-(CH_2)_{\overline{z}}\overset{O}{\overset{\|}{C}}-O^- \quad (IV)$$

wherein:

$R_{11}$, is chosen from polymerizable unsaturated groups such as, for example, acrylates, methacrylates, acrylamides, and methacrylamides, y and z, which may be identical or different, are each chosen from integers ranging from 1 to 3, $R_{12}$ and $R_{13}$, which may be identical or different, are each chosen from hydrogen and methyl, ethyl, and propyl groups, $R_{14}$ and $R_{15}$, which may be identical or different, are each chosen from hydrogen and alkyl groups, provided that the sum of the carbon atoms in $R_{14}$ and $R_{15}$ does not exceed 10.

The polymers comprising such zwitterionic units may also comprise at least one unit derived from non-zwitterionic monomers, such as units chosen from dimethylaminoethyl acrylate, dimethylaminoethyl methacrylate, diethylaminoethyl acrylate, diethylaminoethyl methacrylate, alkyl acrylates, alkyl methacrylates, alkyl acrylamides, alkyl methacrylamides and vinyl acetate.

Other non-limiting examples include the copolymer of methyl methacrylate/dimethyl carboxymethylammonio methyl ethylmethacrylate such as the product sold under the name Diaformer Z301 by the company Sandoz.

(5) Amphoteric fixing polymers derived from chitosan comprising at least one monomeric unit chosen from the following formulae:

(D)

(E)

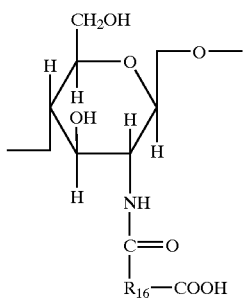

(F)

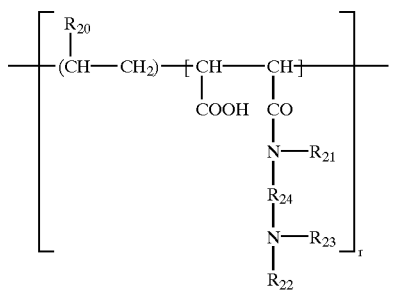

(VI)

wherein the unit (D) is present in an amount generally ranging from 0% to 30%, by weight relative to the total weight of said polymer, the unit (E) is present in an amount generally ranging from 5% to 50%, by weight relative to the total weight of said polymer, and the unit (F) is present in an amount generally ranging from 30% to 90%, by weight relative to the total weight of said polymer, and wherein in said unit (F), $R_{16}$ chosen from groups of formula:

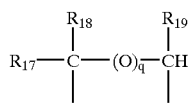

wherein:

q is equal to 0 or 1, and (i) when q is equal to 0, $R_{17}$, $R_{18}$ and $R_{19}$, which may be identical or different, are each chosen from hydrogen, methyl groups, hydroxyl groups, acetoxy groups, amino groups, monoalkylamine groups, dialkylamine groups and alkylthio groups, provided that at least one of the $R_{17}$, $R_{18}$ and $R_{19}$ groups is hydrogen;

When monoalkylamine and dialkylamine groups are used they may be optionally interrupted by at least one nitrogen atom and/or optionally substituted with at least one group chosen from amine, hydroxyl, carboxyl, alkylthio and sulfonic groups.

When alkylthio groups are used, the alkyl portion of said alkylthio group carries an amino group; and (ii) when q is equal to 1, $R_{17}$, $R_{18}$ and $R_{19}$ are each chosen from hydrogen;

Other non-limiting examples include the salts formed by these polymers (5) with bases and acids.

(6) Polymers derived from the N-carboxyalkylation of chitosan, such as, for example, N-carboxymethylchitosan and N-carboxybutylchitosan sold under the name "Evalsan" by the company Jan Dekker.

(7) Amphoteric fixing polymers of the formula (VI), which are described, for example, in French patent 1,400,366, the disclosure of which is incorporated herein by reference:

wherein:

r is chosen such that the number average molecular weight of said polymer ranges from 500 to 6,000,000, such as from 1,000 to 1,000,000;

$R_{20}$ is chosen from hydrogen, $CH_3O$, $CH_3CH_2O$ and phenyl groups;

$R_{21}$ is chosen from hydrogen and lower alkyl groups such as, for example, methyl and ethyl groups;

$R_{22}$ is chosen from hydrogen and lower alkyl groups such as, for example, methyl and ethyl groups;

$R_{23}$ is chosen from lower alkyl groups such as, for example, methyl and ethyl groups, and groups of the formula: $—R_{24}—N(R_{22})_2$, wherein $R_{24}$ is chosen from $—CH_2—CH_2—$, $—CH_2—CH_2—CH_2—$ and $—CH_2—CH(CH_3)—$ groups and $R_{22}$ is defined above;

Other examples include the higher homologues of these groups including higher homologues comprising up to 6 carbon atoms.

(8) Amphoteric fixing polymers of the type —D—X—D—X chosen from:

a) polymers derived from the reaction of at least one compound chosen from chloroacetic acid and sodium chloroacetate with at least one compound comprising at least one unit of formula (XVII):

$$—D—X—D—X—D—$$ (VII)

wherein D is a group:

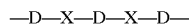

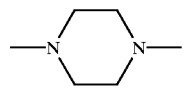

and X is chosen from the symbols E and E', which may be identical or different, wherein E and E' are each chosen from bivalent groups chosen from alkylene groups comprising at least one chain chosen from linear and branched chains comprising up to 7 carbon atoms in the principal chain, and wherein at least one chain may be optionally substituted with at least one hydroxyl group and may comprise 1 to 3 rings chosen from aromatic and heterocyclic rings, and may optionally comprise at least one atom chosen from oxygen, nitrogen and sulfur atoms;

wherein:

the at least one optional atom is present in the form of at least one group chosen from ether, thioether, sulfoxide, sulfone, sulfonium, alkylamine alkenylamine, hydroxyl, benzylamine, amine oxide, quaternary ammonium, amide, imide, alcohol, ester and urethane groups.

b) Polymers of formula:

$$—D—X—D—X—$$ (VII')

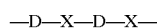

wherein D is:

and X is chosen from the symbols E and E' and wherein at least one X is chosen from E' wherein:

E is chosen from bivalent groups chosen from alkylene groups comprising at least one chain chosen from linear and branched chains comprising up to 7 carbon atoms in the principal chain, and wherein at least one chain may be optionally substituted with at least one hydroxyl group and may comprise 1 to 3 rings chosen from aromatic and heterocyclic rings, and may optionally comprise at least one atom chosen from oxygen, nitrogen and sulfur atoms; wherein:

the at least one optional atom is present in the form of at least one group chosen from ether, thioether, sulfoxide, sulfone, sulfonium, alkylamine alkenylamine, hydroxyl, benzylamine, amine oxide, quaternary ammonium, amide, imide, alcohol, ester and urethane groups, and E' is a bivalent group chosen from alkylene groups comprising at least one chain chosen from linear and branched chains comprising up to 7 carbon atoms in the principal chain, wherein said at least one chain is optionally substituted with at least one hydroxyl group and wherein said at least one chain comprises at least one nitrogen atom substituted with an alkyl chain, wherein said alkyl chain is optionally interrupted by an oxygen atom and, wherein said alkyl chain comprises at least one functional group chosen from carboxyl and hydroxyl functional groups, and wherein said at least one alkyl chain is betainized by reaction with a reactant chosen from chloroacetic acid and sodium chloroacetate.

(9) ($C_1$–$C_5$)alkyl vinyl ether/maleic anhydride copolymers partially modified by semiamidation with an N,N-dialkylaminoalkylamine such as, for example, N,N-dimethylaminopropylamine. These copolymers may also be partially modified by semiesterification with at least one N,N-dialkanolamine. These copolymers may additionally comprise other vinyl units such as, for example, vinylcaprolactam.

Non-limiting examples of fixing polymers according to those of family (3) above include the copolymers with the CTFA name of Octylacrylamide/acrylates/butylaminoethyl methacrylate copolymer, such as the products sold under the names Amphomer, Amhomer LV 71 and Lovocryl 47 by National Starch. Non-limiting examples of fixing polymers according to those of family (4) above include methyl methacrylate/methyl dimethylcarboxymethylammonioethyl methacrylate copolymers, for example those sold under the name Diaformer Z301 by Sandoz.

The nonionic fixing polymers which can be used according to the present invention may be, for example, chosen from:

vinylpyrrolidone homopolymers;

copolymers of vinylpyrrolidone and of vinyl acetate;

polyalkyloxazolines, such as the polyethyloxazolines provided by Dow Chemical under the names Peox 50,000, Peox 200,000 and Peox 500,000;

vinyl acetate homopolymers, such as the product provided under the name of Appretan EM by Hoechst and the product provided under the name of Rhodopas A 012 by Rhône-Poulenc (now Rhodia);

copolymers of vinyl acetate and of acrylic ester, such as the product provided under the name of Rhodopas AD 310 by Rhône-Poulenc (now Rhodia);

copolymers of vinyl acetate and of ethylene, such as the product provided under the name of Appretan TV by Hoechst;

copolymers of vinyl acetate and of maleic ester, for example of dibutyl maleate, such as the product provided under the name of Appretan MB Extra by Hoechst;

copolymers of polyethylene and of maleic anhydride;

alkyl acrylate homopolymers and alkyl methacrylate homopolymers, such as the product provided under the name Micropearl RQ 750 by Matsumoto and the product provided under the name Luhydran A 848 S by BASF;

acrylic ester copolymers, such as, for example, copolymers of alkyl acrylates and of alkyl methacrylates, such as the products provided by Rohm & Haas under the names Primal AC-261 K and Eudragit NE 30 D, by BASF under the names Acronal 601 and Luhydran LR 8833 and 8845, and by Hoechst under the names Appretan N 9213 and N9212;

copolymers of acrylonitrile and of a nonionic unit chosen, for example, from butadiene and alkyl (meth)acrylates; mention may be made of the products provided under the names Nipol LX 531 B by Nippon Zeon and those provided under the name CJ 0601 B by Rohm & Haas;

polyurethanes, such as the products provided under the names Acrysol RM 1020 and Acrysol RM 2020 by Rohm & Haas and the products Uraflex XP 401 UZ and Uraflex XP 402 UZ by DSM Resins;

copolymers of alkyl acrylate and of urethane, such as the product 8538-33 provided by National Starch;

polyamides, such as the product Estapor LO 11 provided by Rhône-Poulenc (now Rhodia);

chemically modified and unmodified nonionic guar gums. The unmodified nonionic guar gums may include, for example, the products sold under the name Vidogum GH 175 by Unipectine and products sold under the name Jaguar C by Meyhall.

The modified nonionic guar gums which may be used according to the invention may, for example, include those modified by $C_1$–$C_6$ hydroxyalkyl groups. Mention may also be made, by way of example, of the hydroxymethyl, hydroxyethyl, hydroxypropyl and hydroxybutyl groups.

These guar gums are known in the art and may, for example, be prepared by reacting the corresponding alkene oxides, such as, for example, propylene oxide, with guar gum, so as to obtain a guar gum modified by hydroxypropyl groups.

Such nonionic guar gums optionally modified by hydroxyalkyl groups are, for example, sold under the trade names Jaguar HP8, Jaguar HP60, Jaguar HL120, Jaguar DC 293, and Jaguar HP 105 by Meyhall and under the name Galactasol 4H4FD2 by Aqualon.

The alkyl radicals of the nonionic polymers comprise from 1 to 6 carbon atoms, unless otherwise mentioned.

Other non-limiting examples of nonionic polymers which are suitable for the preparation of the compositions in accordance with the invention include those chosen from:

vinyllactam copolymers, such as, for example, copolymers of vinylpyrrolidone and of vinyl acetate and vinylpyrrolidone/vinyl acetate/vinyl propionate copolymers the polyvinylcaprolactam Luviskol Plus (BASF)

vinyl acetate homopolymers, such as Appretan EM (Hoechst) and Rhodopas A 012 (Rhône-Poulenc) (now Rhodia)

polyalkyloxazolines, such as Peox 50,000 and Peox 500,000 (Dow Chemical)

copolymers of vinyl acetate and of acrylic ester, such as Rhodopas AD 310 (Rhône-Poulenc) (now Rhodia)

copolymers of vinyl acetate and of ethylene, such as Appretan TV (Hoechst)

copolymers of vinyl acetate and of maleic ester, such as Appretan MB Extra (Hoechst)

alkyl acrylate homopolymers and alkyl methacrylate homopolymers, such as Luhydran A 848 S (BASF)

acrylic ester copolymers, such as Primal AC-261 K (Rohm & Haas), Acronal 601 (BASF) and Appretan N 9213 (Hoechst)

copolymers of acrylonitrile and of a nonionic unit, such as CJ 0601 B (Rohm & Haas)

polyurethanes, such as Acrysol RM 1020 and Acrysol RM 2020 (Rohm & Haas)

copolymers of alkyl acrylate and of urethane, such as 8538-33 (National Starch)

polyamides, such as Estapor LO 11 (Rhône-Poulenc) (now Rhodia).

According to the invention, it is also possible to use at least one fixing polymer of grafted silicone type comprising a polysiloxane portion and a portion comprising a non-silicone organic chain, one of the two portions comprising the main chain of the polymer and the other being grafted onto the main chain. These polymers are disclosed, for example, in Patent Applications EP-A-0,412,704, EP-A-0,412,707, EP-A-0,640,105, WO 95/00578, EP-A-0,582,152, and WO 93/23009 and Patents U.S. Pat. No. 4,693,935, U.S. Pat. No. 4,728,571, and U.S. Pat. No. 4,972,037, the disclosures of which are incorporated herein by reference. These polymers may, for example, be chosen from anionic and nonionic polymers.

Such polymers are, for example, copolymers which may be obtained by radical polymerization of a monomer composition comprising:

a) from 50% to 90% by weight of tert-butyl acrylate;
b) from 0% to 40% by weight of acrylic acid; and
c) from 5% to 40% by weight of silicone macromer of formula:

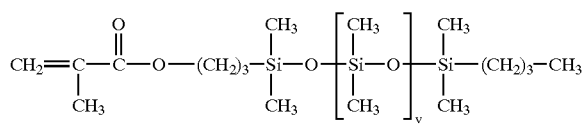

wherein v is a number ranging from 5 to 700, the weight percentages being relative to the total weight of the monomers.

Other examples of grafted silicone polymers include polydimethylsiloxanes (PDMSs) onto which are grafted, via a connecting link of thiopropylene type, at least one mixed polymer unit of poly(meth)acrylic acid type and of at least one mixed polymer unit of poly(alkyl (meth)acrylate) type; and polydimethylsiloxanes (PDMSs) on which are grafted, via a connecting link of thiopropylene type, at least one polymer unit of poly(isobutyl (meth)acrylate) type.

At least one fixing polymer may also be chosen from at least one polyurethane chosen from functionalized polyurethanes and nonfunctionalized polyurethanes wherein said at least one polyurethane may optionally comprise at least one silicone.

According to the invention, the at least one fixing polymer may, for example, be present in an amount generally ranging from 0.1% to 10% by weight, such as from 0.5% to 5% by weight, relative to the total weight of the final composition.

According to the invention, it is also possible to use at least one beneficial agent. The at least one beneficial agent may, for example, be chosen from cationic polymers; cationic surfactants; ceramides and ceramide derivatives; vegetable, mineral and synthetic oils; fatty alcohols and esters; mineral, animal, vegetable and synthetic waxes; and silicones.

The at least one beneficial agent may, for example, be chosen from synthetic oils, such as polyolefins; mineral oils; vegetable oils; fluorinated and perfluorinated oils; natural and synthetic waxes; silicones; cationic polymers; compounds of ceramide type; cationic surfactants; fatty amines; fatty acids and fatty acid derivatives; and fatty alcohols and fatty alcohol derivatives.

The at least one beneficial agent according to the invention may, for example, be chosen from cationic polymers and silicones.

The synthetic oils may, for example, include polyolefins, such as poly-α-olefins and may also include:

synthetic oils of hydrogenated and nonhydrogenated polybutene type, such as hydrogenated and nonhydrogenated polyisobutene.

Other non-limiting examples include isobutylene oligomers with a molecular weight of less than 1000 and combinations of isobutylene oligomers with polyisobutylenes with a molecular weight of greater than 1000, for example, between 1000 and 15,000.

Mention may also be made, as examples of poly-α-olefins which can be used in the context of the present invention, of the polyisobutenes sold under the name of Permethyl 99 A, 101 A, 102 A, 104 A (n=16) and 106 A (n=38) by Presperse Inc. and alternatively the products sold under the name of Arlamol HD (n=3) by ICI (n denoting the degree of polymerization), of hydrogenated and nonhydrogenated polydecene type.

Such products are sold, for example, under the names Ethylflo by Ethyl Corp. and Arlamol PAO by ICI.

The mineral oils which may be used in the compositions of the invention may, for example, be chosen from the group formed by:

hydrocarbons, such as hexadecane and liquid paraffin.

The animal and vegetable oils may, for example, be chosen from sunflower, maize, soybean, avocado, jojoba, cucumber, grape seed, sesame and hazelnut oils; fish oils; glyceryl tricaprate/caprylate; and vegetable and mineral oils of formula $R_9COOR_{10}$ in which $R_9$ represents a higher fatty acid comprising from 7 to 29 carbon atoms, and $R_{10}$ represents a chain chosen from linear and branched hydrocarbon-based chains comprising from 3 to 30 carbon atoms, such as a chain chosen from alkyl and alkenyl chains, for example purcellin oil and liquid jojoba wax.

Use may also be made of natural and synthetic essential oils, such as, for example, eucalyptus, lavendin, lavender, vetiver, litsea cubeba, lemon, sandalwood, rosemary, camomile, savory, nutmeg, cinnamon, hyssop, caraway, orange, geraniol, cade and bergamot oils.

The waxes may be chosen from natural substances (from animals and vegetables) and synthetic substances which are solid at ambient temperature (20°–25° C.). They are insoluble in water, are soluble in oils and are capable of forming a water-repellent film.

Reference may be made, on the definition of waxes, to, for example, P. D. Dorgan, Drug and Cosmetic Industry, December 1983, pp. 30–33, the disclosure of which is incorporated herein by reference.

The waxes may, for example, be chosen from carnauba wax; candelilla wax; esparto wax; paraffin wax; ozokerite; vegetable waxes, such as olive tree wax, rice wax, hydrogenated jojoba wax and absolute flower waxes, such as the blackcurrant flower essential wax sold by Bertin (France); and animal waxes, such as beeswaxes and modified beeswaxes (cerabellina); other waxes and waxy raw materials which may be used according to the invention include, for example, marine waxes, such as that sold by Sophim under the reference M82, polyethylene waxes and polyolefin waxes in general.

According to the present invention, at least one cationic polymer may be used as a beneficial agent. The at least one cationic polymer may be chosen from any of those already known to improve at least one cosmetic property of hair treated with detergent compositions, such as, for example, those described in patent application EP-A-0 337,354 and in French patent applications FR-A-2 270,846, 2,383,660, 2,598,611, 2,470,596 and 2,519,863, the disclosures of which are incorporated herein by reference.

As used herein, "cationic polymer" refers to polymers chosen from polymers comprising at least one cationic group and polymers comprising at least one group which can be ionized to form cationic groups.

According to the present invention, the at least one cationic polymer may be chosen from polymers which comprise at least one unit comprising at least one group chosen from primary amine groups, secondary amine groups, tertiary amine groups and quaternary amine groups, wherein said at least one group forms part of the polymer skeleton, or is carried by at least one lateral substituent on said polymer skeleton.

According to the present invention, the at least one cationic polymer has a number-average molecular mass ranging for example from 500 to $5 \times 10^6$, such as from $1 \times 10^3$ to $3 \times 10^6$.

The at least one cationic polymer may be chosen from polymers of quaternary polyammonium, polymers of polyamino amide, and polymers of polyamine. Such polymers are known in the art.

For example, polymers of quaternary polyammonium, polymers of polyamino amide, and polymers of polyamine, which can be used in accordance with the present invention comprise the polymers described in French patents Nos. 2,505,348 and 2,542,997, the disclosures of which are incorporated herein. Non-limiting examples of such polymers include:

(1) Homo- and co-polymers derived from at least one monomer chosen from acrylic esters, methacrylic esters and amides, wherein said homo- and co-polymers comprise at least one unit chosen from units of formulae:

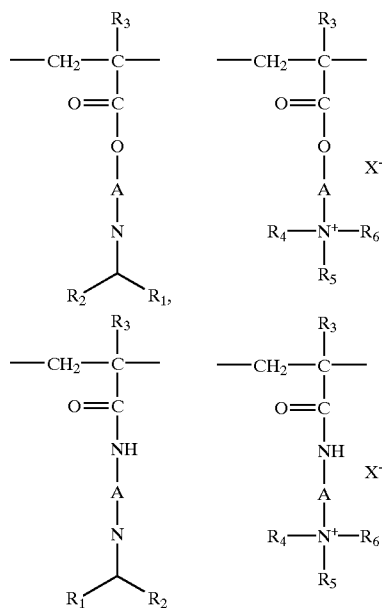

wherein:
$R_3$, which may be identical or different, are each chosen from a hydrogen atom and a $CH_3$ group;
A, which may be identical or different, are each chosen from linear and branched alkyl groups comprising from 1 to 6 carbon atoms, such as 2 or 3 carbon atoms, and hydroxyalkyl groups comprising from 1 to 4 carbon atoms;
$R_4$, $R_5$ and $R_6$, which may be identical or different, are each chosen from alkyl groups comprising from 1 to 18 carbon atoms, such as from 1 to 6 carbon atoms, and benzyl groups;
$R_1$ and $R_2$, which may be identical or different, are each chosen from a hydrogen atom and alkyl groups comprising from 1 to 6 carbon atoms, such as methyl and ethyl; and
$X^-$ is an anion chosen from anions derived from at least one inorganic acid and anions derived from at least one organic acid, such as methosulfate anions, and halide anions, such as chloride anions and bromide anions.

Copolymers of family (1) may further comprise at least one unit derived from at least one comonomer chosen from acrylamides, methacrylamides, diacetone acrylamides, acrylamides and methacrylamides, wherein said at least one comonomer is substituted on the nitrogen with at least one group chosen from ($C_1$–$C_4$) alkyls, acrylic acids, methacrylic acids, acrylic esters, methacrylic esters, vinyllactams and vinyl esters. Non-limiting examples of vinyllactams include vinylpyrrolidone and vinylcaprolactam.

Non-limiting examples of suitable copolymers include:
copolymers derived from at least one monomer of (i) acrylamide and (ii) dimethylaminoethyl methacrylate quaternized with at least one group chosen from dimethyl sulfate and dimethyl halide, such as the product sold under the name Hercofloc by the company Hercules;
copolymers derived from at least one monomer of (i) acrylamide and (ii) methacryloyloxyethyltrimethylammonium chloride described, for example, in patent application EP-A-080,976, the disclosure of which is incorporated herein by reference, and which is sold under the name Bina Quat P 100 by the company Ciba Geigy;

copolymers derived from at least one monomer of (i) acrylamide and (ii) methacryloyloxyethyltrimethylammonium methosulfate, such as, for example, copolymers sold under the name Reten by the company Hercules;

quaternized and non-quaternized vinylpyrrolidone/ dialkylaminoalkyl acrylate copolymers and quaternized and non-quaternized vinylpyrrolidone/ dialkylaminoalkyl methacrylate copolymers, such as the products sold under the name "Gafquat" by the company ISP, such as, for example, "Gafquat 734" and "Gafquat 755" and the products known as "Copolymer 845, 958 and 937". These polymers are described in detail in French patents 2,077,143 and 2,393,573, the disclosures of which are incorporated herein by reference;

dimethylaminoethyl methacrylate/vinylcaprolactam/ vinylpyrrolidone terpolymers, such as the product sold under the name Gaffix VC 713 by the company ISP;

vinylpyrrolidone/methacrylamidopropyldimethylamine copolymers, such as the product sold under the name Styleze CC 10 by ISP; and quaternized vinylpyrrolidone/ dimethylaminopropylmethacrylamide copolymers, such as the product sold under the name "Gafquat HS 100" by the company ISP.

(2) Cellulose ether derivatives comprising quaternary ammonium groups, such as those described in French patent 1,492,597, the disclosure of which is incorporated herein by reference, and polymers sold under the names "JR" (JR 400, JR 125 and JR 30M) and "LR" (LR 400 and LR 30M) by the company Union Carbide Corporation. These polymers are also defined in the CTFA dictionary as quaternary ammoniums of hydroxyethylcellulose which have reacted with an epoxide substituted with a trimethylammonium group.

(3) Cationic cellulose derivatives such as cellulose copolymers and cellulose derivatives grafted with at least one water-soluble monomer of quaternary ammonium, such as those described in U.S. Pat. No. 4,131,576, the disclosure of which is incorporated herein by reference, such as hydroxyalkylcelluloses (such as, for example, hydroxymethylcelluloses, hydroxyethylcelluloses and hydroxypropylcelluloses, wherein said hydroxyalkylcelluloses are grafted with at least one salt chosen from, for example, methacryloylethyltrimethylammonium salts, methacrylamidopropyltrimethylammonium salts and dimethyldiallylammonium salts). For example, commercial products corresponding to the aforementioned cationic cellulose derivatives include the products sold under the names "Celquat L 200" and "Celquat H 100" by the company National Starch.

(4) Cationic polysaccharides, such as those described in U.S. Pat. Nos. 3,589,578 and 4,031,307, the disclosures of which are incorporated herein by reference, such as guar gums comprising at least one cationic trialkylammonium group. For example, guar gums modified with at least one salt, such as a chloride salt, of 2,3-epoxypropyltrimethylammonium may be used in the present invention. Such products are sold for example under the trade names Jaguar C13 S, Jaguar C 15, Jaguar C 17 and Jaguar C162 by the company Meyhall.

(5) Polymers comprising (i) at least one piperazinyl unit and (ii) at least one group chosen from divalent alkylene groups and divalent hydroxyalkylene groups, wherein said at least one group optionally comprises at least one chain chosen from straight chains and branched chains, wherein said at least one chain is optionally interrupted by at least one entity chosen from oxygen atoms, sulfur atoms, nitrogen atoms, aromatic rings and heterocyclic rings, the oxidation products of said polymers and the quaternization products of said polymers. For example, such polymers are described in French patents 2,162,025 and 2,280,361, the disclosures of which are incorporated herein by reference.

(6) Water-soluble polyamino amides which may be prepared via at least one polycondensation reaction of at least one acidic compound and at least one polyamine compound, wherein said polyamino amides may be crosslinked with at least one crosslinking agent chosen from epihalohydrins, diepoxides, dianhydrides, unsaturated dianhydrides, bis-unsaturated derivatives, bis-halohydrins, bis-azetidiniums, bis-haloacyidiamines, bis-alkyl halides and oligomers derived from reaction of at least one difunctional compound with at least one compound chosen from bis-halohydrins, bis-azetidiniums, bis-haloacyldiamines, bis-alkyl halides, epihalohydrins, diepoxides and bis-unsaturated derivatives, wherein said crosslinking agent may be used in a proportion ranging for example from 0.025 mol to 0.35 mol per amine group of said polyamino amide, wherein said polyamino amides may optionally be alkylated, and wherein if said polyamino amides comprise at least one tertiary amine group, said polyamino amides may optionally be quaternized. For example, such polymers are described in French patents 2,252,840 and 2,368,508, the disclosures of which are incorporated herein by reference.

(7) Polyamino amide derivatives derived from condensation of at least one polyalkylene polyamine with at least one polycarboxylic acid, followed by alkylation with at least one difunctional agent.

Non-limiting examples of such polyamino amide derivatives include adipic acid/ dialkylaminohydroxyalkyldialkylenetriamine polymers wherein the alkyl group comprises from 1 to 4 carbon atoms, such as methyl groups, ethyl groups and propyl groups. For example, such polymers are described in French patent 1,583,363, the disclosure of which is incorporated herein by reference.

Other non-limiting examples of such derivatives include the adipic acid/dimethylaminohydroxypropyl/ diethylenetriamine polymers sold under the names "Cartaretine F, F4, and F8" by the company Sandoz.

(8) Polymers derived from reaction of (i) at least one polyalkylene polyamine comprising two primary amine groups and at least one secondary amine group with (ii) at least one dicarboxylic acid chosen from diglycolic acid and saturated aliphatic dicarboxylic acids comprising from 3 to 8 carbon atoms. According to the present invention, the molar ratio of the at least one polyalkylene polyamine to the at least one dicarboxylic acid ranges for example from 0.8:1 to 1.4:1. The polyamino amide resulting from the above reaction may be reacted with epichlorohydrin in a molar ratio of epichlorohydrin to the at least one secondary amine group of the polyamino amide ranging for example from 0.5:1 to 1.8:1. For example, such polymers are described in U.S. Pat. Nos. 3,227,615 and 2,961,347, the disclosures of which are incorporated herein by reference.

Polymers of this type are sold for example under the name "Hercosett 57" by the company Hercules Inc. and under the names "PD 170" and "Delsette 101" by the company Hercules in the case of adipic acid/epoxypropyl/diethylenetriamine copolymers.

(9) Cationic polymers chosen from cyclopolymers of alkyldiallylamine and cyclopolymers of dialkyldiallylammonium, such as homopolymers and copolymers comprising, as the main constituent of the chain, at least one unit chosen from units of formulae (VI) and (VI'):

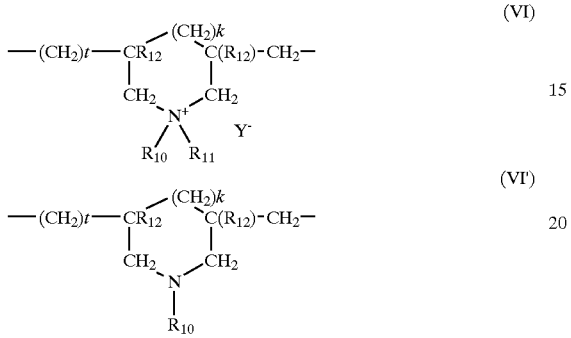

wherein:

k and t, which may be identical or different, are each chosen from 0 and 1, with the proviso that the sum of k+t is equal to 1;

$R_{12}$, which may be identical or different, are each chosen from a hydrogen atom and a methyl group;

$R_{10}$ and $R_{11}$, which may be identical or different, are each chosen from alkyl groups comprising from 1 to 22 carbon atoms, hydroxyalkyl groups wherein the alkyl portion of said hydroxyalkyl group optionally comprises from 1 to 5 carbon atoms, lower $C_1$–$C_4$ amidoalkyl groups, and, in addition, $R_{10}$ and $R_{11}$, together with the nitrogen cation to which they are commonly attached, form at least one cationic heterocyclic group, such as cationic piperidyl groups and cationic morpholinyl groups;

$Y^-$ is an anion, such as bromide, chloride, acetate, borate, citrate, tartrate, bisulfate, bisulfite, sulfate and phosphate. For example, such polymers are described in French patent 2,080,759 and in its Certificate of Addition 2,190,406, the disclosures of which are incorporated herein by reference.

In one embodiment, $R_{10}$ and $R_{11}$, which may be identical or different, are each chosen from alkyl groups comprising from 1 to 4 carbon atoms.

Non-limiting examples of the polymers defined above include the dimethyldiallyl-ammonium chloride homopolymer sold under the name "Merquat 100" by the company Calgon (and its homologues of low weight-average molecular mass) and copolymers of diallyldimethylammonium chloride and of acrylamide, sold under the name "Merquat 550".

(10) Quaternary diammonium polymers comprising at least two repeating units of formula:

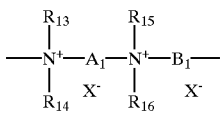

wherein:

$R_{13}$, $R_{14}$, $R_{15}$ and $R_{16}$ which may be identical or different, can each be chosen from aliphatic groups comprising from 1 to 20 carbon atoms, alicyclic groups comprising from 3 to 20 carbon atoms, arylaliphatic groups comprising from 4 to 20 carbon atoms, and lower hydroxyalkylaliphatic groups, and in addition $R_{13}$, $R_{14}$, $R_{15}$ and $R_{16}$, separately or at least two of which together, with the nitrogen cations to which they are attached, can each form at least one cationic heterocycle optionally comprising an additional heteroatom other than nitrogen, and in addition $R_{13}$, $R_{14}$, $R_{15}$ and $R_{16}$, which may be identical or different, can each be chosen from linear and branched $C_1$–$C_6$ alkyl groups substituted with at least one group chosen from nitrile groups, ester groups, acyl groups, amide groups and groups chosen from groups of formulae —CO—O—$R_{17}$—D and —CO—NH—$R_{17}$—D, wherein $R_{17}$ is chosen from alkylene groups and D is chosen from quaternary ammonium groups;

$A_1$ and $B_1$, which may be identical or different, are each chosen from polymethylene groups comprising from 2 to 20 carbon atoms chosen from linear and branched, saturated and unsaturated polymethylene groups wherein said polymethylene groups may optionally comprise, optionally linked to and optionally intercalated in the main chain, at least one entity chosen from aromatic rings, oxygen atoms, sulfur atoms, sulfoxide groups, sulfone groups, disulfide groups, amino groups, alkylamino groups, hydroxyl groups, quaternary ammonium groups, ureido groups, amide groups and ester groups; and $X^-$ is an anion chosen from anions derived from inorganic acids and anions derived from organic acids; and $A_1$, $R_{13}$ and $R_{15}$ may optionally form, together with the two quaternized nitrogen atoms to which they are attached, at least one quaternized piperazine ring;

with the proviso that if $A_1$ is chosen from linear and branched, saturated and unsaturated polymethylene groups and linear and branched, saturated and unsaturated hydroxypolymethylene groups, $B_1$ may also be chosen from groups of formula:

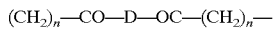

wherein:

n is a number such that the overall quaternary diammonium polymer has a number average molecular weight ranging from 1000 to 100,000; and D is chosen from:

a) glycol residues of formula: —O—Z—O—, wherein Z is chosen from linear and branched hydrocarbon groups and groups chosen from groups of formulae:

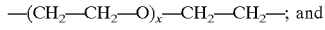

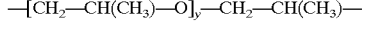

wherein x and y, which may be identical or different, are each chosen from integers ranging from 1 to 4 (in which case x and y represent a defined and unique degree of polymerization) and any number ranging from 1 to 4 (in which case x and y represent an average degree of polymerization);

b) bis-secondary diamine residues such as piperazine derivatives;

c) bis-primary diamine residues chosen from residues of formula: —NH—Y—NH—, wherein Y is chosen from linear and branched hydrocarbon groups and residues of formula

—CH$_2$—CH$_2$—S—S—CH$_2$—CH$_2$—;

and d) ureylene groups of formula: —NH—CO—NH— wherein n in the above formula ranges from 1 to 6.

In one embodiment, X$^-$ is an anion chosen from chloride ions and bromide ions.

According to the present invention, the quaternary diammonium polymers have a number-average molecular mass ranging for example from 1000 to 100,000.

For example, polymers of this type are described in French Patent Nos. 2,320,330, 2,270,846, 2,316,271, 2,336,434 and 2,413,907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020, the disclosures of which are incorporated herein by reference.

Further, according to the present invention, polymers comprising at least two repeating units of formula (a) may be used:

$$-\underset{\underset{R_2}{|}}{\overset{\overset{R_1}{|}}{N^+}}-(CH_2)_n-\underset{\underset{R_4}{|}}{\overset{\overset{R_3}{|}}{N^+}}-(CH_2)_p-\quad\quad (a)$$
$$\quad\quad X^-\quad\quad\quad X^-$$

wherein:

$R_1$, $R_2$, $R_3$ and $R_4$, which may be identical or different, are each chosen from alkyl groups comprising from 1 to 4 carbon atoms and hydroxyalkyl groups comprising from 1 to 4 carbon atoms;

n and p, which may be identical or different, are each chosen from integers ranging from 2 to 20; and X$^-$ is an anion chosen from anions derived from inorganic acids and anions derived from organic acids.

In one embodiment, $R_1$, $R_2$, $R_3$ and $R_4$ are chosen from methyl groups, n=3, p=6 and X$^-$=Cl$^-$. This unit is commonly known as Hexadimethrine chloride according to INCI (CTFA) nomenclature.

(11) Cationic polymers chosen from polyquaternary ammonium polymers comprising units of formula (VIII):

$$-\underset{\underset{R_{19}}{|}}{\overset{\overset{R_{18}}{|}}{N^+}}-(CH_2)_r-NH-CO-(CH_2)_q-CO-NH-(CH_2)_s-\underset{\underset{R_{21}}{|}}{\overset{\overset{R_{20}}{|}}{N^+}}-A-\quad\quad (VIII)$$
$$X^-\quad\quad\quad\quad\quad\quad\quad\quad\quad\quad\quad\quad X^-$$

wherein:

$R_{18}$, $R_{19}$, $R_{20}$ and $R_{21}$, which may be identical or different, are each chosen from a hydrogen atom, a methyl group, an ethyl group, a propyl group, a β-hydroxyethyl group, a β-hydroxypropyl group and —CH$_2$CH$_2$(OCH$_2$CH$_2$)$_p$ OH groups wherein p is an integer ranging from 0 to 6, with the proviso that $R_{18}$, $R_{19}$, $R_{20}$ and $R_{21}$ are all not simultaneously chosen from a hydrogen atom;

r and s, which may be identical or different, are each chosen from integers ranging from 1 to 6;

q is an integer ranging from 1 to 34;

X$^-$ is an anion, such as a halide; and

A is chosen from dihalide groups and groups of formula —CH$_2$—CH$_2$—O—CH$_2$—CH$_2$—.

For example, such compounds are described in patent application EP-A-122,324, the disclosure of which is incorporated by reference.

Non-limiting examples of the polyquarternary ammonium polymers are "Mirapol® A 15", "Mirapol® AD1", "Mirapol® AZ1" and "Mirapol® 175" sold by the company Miranol.

(12) Quaternary polymers of vinylpyrrolidone and quaternary polymers of vinylimidazole, such as, for example, the products sold under the names Luviquat® FC 905, FC 550 and FC 370 by the company BASF.

(13) Polyamines, such as Polyquart® H sold by Henkel under the reference name "Polyethylene glycol (15) Tallow polyamine" in the CTFA dictionary.

(14) Crosslinked (meth)acryloyloxy(C$_1$–C$_4$)alkyltri (C$_1$–C$_4$)alkylammonium salt polymers, such as the polymers derived from homopolymerization of dimethylaminoethyl methacrylate quaternized with methyl chloride and polymers derived from copolymerization, for example, of acrylamide with dimethylaminoethyl methacrylate quaternized with a methyl chloride, wherein the homo- or copolymerization is followed by crosslinking with at least one compound comprising olefinic unsaturation, such as methylenebisacrylamide. For example, a crosslinked acrylamide/ methacryloyloxyethyltrimethylammonium chloride copolymer (20/80 by weight) in the form of a dispersion comprising 50% by weight of the said copolymer in mineral oil may be used. This dispersion is sold under the name "Salcare® SC 92" by the company Allied Colloids. Further, a crosslinked methacryloyloxyethyltrimethylammonium chloride homopolymer comprising 50% by weight of the homopolymer in mineral oil or in a liquid ester may be used. These dispersions are sold under the names "Salcare® SC 95" and "Salcare® SC 96" by the company Allied Colloids.

Other cationic polymers which may be used as the at least one cationic polymer according to the present invention are cationic proteins, cationic protein hydrolysates, polyalkyleneimines (such as polyethyleneimines), polymers comprising at least one vinylpyridine unit, polymers comprising at least one vinylpyridinium unit, condensates of polyamines, condensates of epichlorohydrin, quaternary polyureylenes, and chitin derivatives.

In certain embodiments of the present invention, the at least one cationic polymer is chosen from quaternary cellulose ether derivatives (such as the products sold under the name "JR 400" by the company Union Carbide Corporation), cationic cyclopolymers (such as the homopolymers and copolymers of dimethyldiallylammonium chloride, sold under the names "Merquat 100", "Merquat 550" and "Merquat S" by the company Calgon), quaternary polymers of vinylpyrrolidone, and quaternary polymers of vinylimidazole.

The beneficial agents of the present invention may comprise at least one silicone.

The at least one silicone may be, for example, chosen from polyorganosiloxanes that are insoluble in the composition. The at least one silicone may be, for example, in the form of at least one composition chosen form of oils, waxes, resins, and gums.

The organopolysiloxanes are defined in more detail in the work by Walter Noll, "Chemistry and Technology of Silicones" (1968) Academic Press, the disclosure of which is incorporated herein by reference.

The at least one silicone may, for example, be chosen from linear volatile silicones comprising 2 to 9 silicon atoms with a kinematic viscosity of up to $5 \times 10^{-6}$ m$^2$/s at 25° C. Examples include, decamethyltetrasiloxane, sold under the name "SH 200" by the company Toray Silicone. Silicones forming part of this category are also described in the article published in Cosmetics and Toiletries, Vol. 91, Jan. 76, p. 27–32, Todd & Byers, "Volatile Silicone Fluids for Cosmetics," the disclosure of which is incorporated herein by reference.

At least one non-volatile silicone can also be used. For example, the at least one non-volatile silicone can be chosen from polyalkylsiloxanes, polyarylsiloxanes, polyalkylarylsiloxanes, silicone gums, silicone resins, and polyorganosiloxanes modified with at least one organofunctional group.

The at least one non-volatile silicone may be chosen from polyalkylsiloxanes, among which may be mentioned polydimethylsiloxanes comprising trimethylsilyl end groups with a kinematic viscosity generally ranging, for example, from $5 \times 10^{-6}$ to 2.5 m$^2$/s at 25° C., such as a kinematic viscosity generally ranging, for example, from $1 \times 10^{-5}$ to 1 m$^2$/s. The kinematic viscosity of the silicones is measured, for example, at 25° C. according to ASTM Standard 445, Appendix C.

Non-limiting examples of polyalkylsiloxanes include the following commercial products:

Silbione oils of the 47 and 70,047 series and Mirasil oils sold by Rhône-Poulenc (now Rhodia), such as, for example, the oil 70,047 V 500,000;

oils of the Mirasil series sold by Rhône-Poulenc (now Rhodia), such as Mirasil DMCO-oil 70 646. Mirasil DMCO-oil 70 646 is a member of a class called Dimethicone Copolyol, the class being defined as a polymer of dimethylsiloxane with polyoxyethylene and/or polyoxypropylene side chains. See International Cosmetic Ingredient Dictionary and Handbook, Seventh Edition, 1997, Volume 1, page 432, the disclosure of which is incorporated by reference herein.;

oils of the 200 series from Dow Corning, such as, for example, DC200 with a kinematic viscosity of 60,000 cSt; and Viscasil oils from General Electric and some oils of the SF series (SF 96, SF 18) from General Electric.

Mention may also be made of Dow Corning 190 Surfactant, also a member of the class called Dimethicone Copolyol as referred to above.

Mention may also be made of polydimethylsiloxanes comprising dimethylsilanol end groups (dimethiconol according to the CTFA name), such as the oils of the 48 series from Rhône-Poulenc (now Rhodia).

Mention may additionally be made of the poly($C_1$–$C_4$) alkylsiloxanes products sold under the names "Abil Wax 9800 and 9801" by Goldschmidt.

The at least one non-volatile silicone may be chosen from polyalkylarylsiloxanes chosen, for example, from linear and branched polydimethylmethylfenylsiloxanes and polydimethyldiphenylsiloxanes, with a kinematic viscosity generally ranging, for example, from $1 \times 10^{-5}$ to $5 \times 10^{-2}$ m$^2$/s at 25° C.

Non-limiting examples of polyalkylarylsiloxanes include products sold under the following names:

Silbione oils of the 70,641 series of Rhône-Poulenc (now Rhodia);

oils of the Rhodorsil 70,633 and 763 series of Rhône-Poulenc (now Rhodia);

the oil Dow Corning 556 Cosmetic Grade Fluid from Dow Corning;

silicones of the PK series of Bayer, such as the product PK20;

silicones of the PN and PH series of Bayer, such as the products PN1000 and PH1000; and some oils of the SF series of General Electric, such as SF 1023, SF 1154, SF 1250 and SF 1265.

The at least one non-volatile silicone may be chosen from silicone gums, for example, polydiorganosiloxanes with high number-average molecular masses generally ranging, for example, from 200,000 to 1,000,000 used alone and in combination with at least one solvent. The at least one solvent can be chosen from, for example, volatile silicones, polydimethylsiloxane (PDMS) oils, polyphenylmethylsiloxane (PPMS) oils, isoparaffins, polyisobutylenes, methylene chloride, pentane, dodecane, and tridecane.

Mention may also, for example, be made of the following products:

polydimethylsiloxane, polydimethylsiloxane/methylvinylsiloxane gums, polydimethylsiloxane/diphenylsiloxane, polydimethylsiloxane/phenylmethylsiloxane, and polydimethylsiloxane/diphenylsiloxane/methylvinylsiloxane.

The at least one non-volatile silicone may be chosen from organopolysiloxane resins which are crosslinked siloxane sytstems comprising at least one unit chosen from:

$R_2SiO_{2/2}$, $R_3SiO_{1/2}$, $RSiO_{3/2}$ and $SIO_{4/2}$, wherein:

R, which may be identical or different, are each chosen from hydrocarbon-based groups comprising 1 to 16 carbon atoms and phenyl groups. For example, in one embodiment R is a $C_1$–$C_4$ alkyl group, such as a methyl group. In another embodiment R is a phenyl group.

Mention may also be made of the product sold under the name "Dow Corning 593" and those sold under the names "Silicone Fluid SS 4230 and SS 4267" by General Electric, which are silicones of dimethyl/trimethylsiloxane structure.

Mention may also be made of resins of the trimethylsiloxysilicate type sold, for example, under the names X22-4914, X21-5034, and X21-5037 by Shin-Etsu.

The at least one non-volatile silicone may be chosen from organomodified silicones as defined above and comprising, in their structure, at least one organofunctional group attached via a hydrocarbon-based radical.

Among the organomodified silicones, mention may be made of polyorganosiloxanes comprising at least one constituent chosen from:

polyethyleneoxy and polypropyleneoxy groups optionally comprising at least one $C_6$–$C_{24}$ alkyl group, such as the products known as dimethicone copolyol sold by Dow Corning under the name DC 1248 and the oils Silwet L 722, L 7500, L 77, and L 711 from Union Carbide and the ($C_{12}$)alkyl methicone copolyol sold by Dow Corning under the name Q2 5200;

substituted and unsubstituted amine groups, such as the products sold under the names GP 4 Silicone Fluid and GP 7100 by Genesee, and the products sold under the names Q2 8220, Dow Corning 929, and Dow Corning 939 by Dow Corning. The substituted aminated groups are, for example, $C_1$–$C_4$ aminoalkyl groups;

thiol groups, such as the products sold under the names "GP 72 A" and "GP 71" from Genesee;

alkoxylated groups, such as the products sold under the name "Silicone Copolymer F-755" by SWS Silicones and "Abil Wax 2428, 2434 and 2440" by Goldschmidt;

hydroxylated groups, such as, for example, the polyorganosiloxanes comprising a hydroxyalkyl functional group disclosed in French Patent Application FR-A-85/16334, the disclosure of which is incorporated herein by reference, corresponding to the formula (IX):

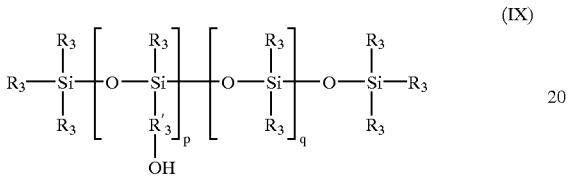

(IX)

wherein:

$R_3$, which may be identical or different, are each chosen from methyl groups and phenyl groups, wherein at least 60 mol % of the $R_3$ groups are methyl;

$R_{13}$ is a divalent hydrocarbon-based $C_2$–$C_{18}$ alkylene link;

p is chosen from integers ranging from 1 to 30; and q is chosen from integers ranging from 1 to 150 acyloxyalkyl groups, such as, for example, the polyorganosiloxanes disclosed in U.S. Pat. No. 4,957,732, the disclosure of which is incorporated herein by reference, corresponding to the formula (X):

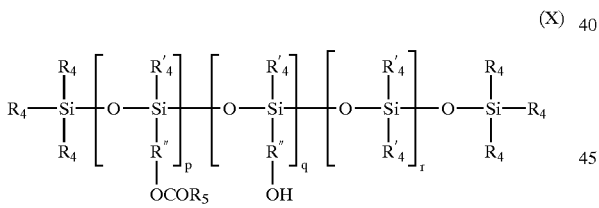

(X)

wherein:

$R_4$, which may be identical or different, are each chosen from methyl, phenyl, —$OCOR_5$ and hydroxyl groups, wherein only one of the $R_4$ groups per silicon atom is OH;

$R'_4$, which may be identical or different, are each chosen from methyl and phenyl groups, wherein at least 60 mol % of the combined $R_4$ and $R'_4$ groups are methyl;

$R_5$ is chosen from $C_8$–$C_{20}$ alkyl and alkenyl groups;

R", which may be identical or different, are each chosen from divalent, linear and branched, hydrocarbon-based $C_2$–$C_{18}$ alkylene radicals;

r is chosen from integers ranging from 1 to 120;

p is chosen from integers ranging from 1 to 30; and q is less than 0.5 p, with the sum p+q ranging from 1 to 30.

The polyorganosiloxanes of formula (X) can comprise:

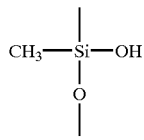

groups in amounts not exceeding 15% of the sum p+q+r;

anionic groups of the carboxyl type, such as, for example, the products from Chisso Corporation described in Patent EP 186,507, the disclosure of which is incorporated herein by reference, and of alkylcarboxyl type, such as those present in the product X-22-3701 E from Shin-Etsu; 2-hydroxyalkylsulfonate type; and 2-hydroxyalkylthiosulfate type, such as the products sold by Goldschmidt under the names "Abil S201" and "Abil S255"; and hydroxyacylamino groups, such as the polyorganosiloxanes described in Application EP 342,834, the disclosure of which is incorporated herein by reference. Mention may be made, for example, of the product Q2-8413 from Dow Corning.

According to the invention, all the silicones may also be used in the form of emulsions, nanoemulsions and microemulsions.

Other non-limiting examples of polyorganosiloxanes include:

nonvolatile silicones chosen from polyalkylsiloxanes comprising trimethylsilyl end groups, such as oils with a kinematic viscosity generally ranging, for example, from 0.2 to 2.5 $m^2$/s at 25° C., such as the oils of the DC200 series from Dow Corning, and further such as oils with a kinematic viscosity of 60,000 cSt, of of the Silbione 70047 series and 47 series and the 70,047 V 500,000 oil sold by Rhône-Poulenc (now Rhodia), polyalkylsiloxanes comprising dimethylsilanol end groups, such as dimethiconols, and polyalkylarylsiloxanes, such as the oil Silbione 70641 V 200 sold by Rhône-Poulenc (now Rhodia);

the organopolysiloxane resin sold under the name Dow Corning 593;

polysiloxanes comprising at least one amine group, such as polysiloxanes chosen from amodimethicones and trimethylsilylamodimethicone.

The cationic proteins and protein hydrolysates are, for example, chemically modified polypeptides comprising at least one quaternary ammonium group. The at least one quaternary ammonium group may be at the chain end and may also be grafted onto the chain. Their molecular mass may vary, generally ranging, for example, from 1,500 to 10,000, such as from 2,000 to 5,000 approximately. Non-limiting examples of these compounds include:

collagen hydrolysates comprising triethylammonium groups, such as the products sold under the name "Quat-Pro E" by Maybrook and named in the CTFA dictionary "Triethonium Hydrolyzed Collagen Ethosulfate";

collagen hydrolysates comprising trimethylammonium and trimethylstearylammonium chloride groups, sold under the name of "Quat-Pro S" by Maybrook and named in the CTFA dictionary "Steartrimonium Hydrolyzed Collagen";

animal protein hydrolysates comprising trimethylbenzylammonium groups, such as the products sold under the name "Crotein BTA" by Croda and named in the CTFA dictionary "Benzyltrimonium Hydrolyzed Animal Protein";

protein hydrolysates comprising, on the polypeptide chain, quaternary ammonium groups comprising at least one alkyl radical comprising 1 to 18 carbon atoms.

Mention may be made, among these protein hydrolysates, of, inter alia:

"Croquat L", the quaternary ammonium groups of which comprise a $C_{12}$ alkyl group;

"Croquat M", the quaternary ammonium groups of which comprise $C_{10}$–$C_{18}$ alkyl groups;

"Croquat S", the quaternary ammonium groups of which comprise a $C_{18}$ alkyl group;

"Crotein Q", the quaternary ammonium groups of which comprise at least one alkyl group comprising from 1 to 18 carbon atoms.

These various products are sold by Croda.

Other quaternized proteins and hydrolysates are, for example, those corresponding to the formula (XI):

wherein:
X⁻ is an anion of an acid chosen from organic and inorganic acids;
A is a protein residue derived from collagen protein hydrolysates;
$R_5$ is a lipophilic group comprising up to 30 carbon atoms; and
$R_6$ is an alkylene group comprising 1 to 6 carbon atoms.

Mention may be made, for example, of the products sold by Inolex under the name "Lexein QX 3000", known in the CTFA dictionary as "Cocotrimonium Collagen Hydrolysate".

Mention may also be made of quaternized plant proteins, such as wheat, maize and soybean proteins; non-limiting examples of quaternized wheat proteins include those sold by Croda under the names "Hydrotriticum WQ and QM", referred to in the CTFA dictionary as "Cocodimonium Hydrolysed Wheat Protein", and "Hydrotriticum QL", referred to in the CTFA dictionary as "Laurdimonium Hydrolysed Wheat Protein", and "Hydrotriticum QS", referred to in the CTFA dictionary as "Steardimonium Hydrolysed Wheat Protein."

According to the present invention, the compounds of ceramide type may be, for example, chosen from ceramides, glycoceramides, pseudoceramides, and neoceramides, which may be chosen from natural and synthetic compounds.

Compounds of ceramide type are, for example, disclosed in Patent Applications DE 4,424,530, DE 4,424,533, DE 4,402,929, DE 4,420,736, WO 95/23807, WO 94/07844, EP-A-0 646 572, WO 95/16665, FR-2,673,179, EP-A-0 227,994 and WO 94/07844, WO 94/24097 and WO 94/10131, the disclosures of which are incorporated herein by reference.

Other non-limiting examples of compounds of ceramide type according to the invention include:
2-(N-linoleoylamino)octadecane-1,3-diol,
2-(N-oleoylamino)octadecane-1,3-diol,
2-(N-palmitoylamino)octadecane-1,3-diol,
2-(N-stearoylamino)octadecane-1,3-diol,
2-(N-behenoylamino)octadecane-1,3-diol,
2-[N-(2-hydroxypalmitoyl)amino]octadecane-1,3-diol,
2-(N-stearoylamino)octadecane-1,3,4-triol and N-stearoylphytosphingosine,
2-(N-palmitoylamino)hexadecane-1,3-diol,
bis(N-hydroxyethyl-N-cetyl)malonamide,
the N-(2-hydroxyethyl)-N-(3-cetyloxy-2-hydroxypropyl) amide of cetylic acid, and
N-docosanoyl-N-methyl-D-glucamine.

Use may also be made of at least one cationic surfactant, non-limiting examples of which include: salts of optionally polyoxyalkylenated primary, secondary and tertiary fatty amines, quaternary ammonium salts, imidazoline derivatives and amine oxides with a cationic nature.

Non-limiting examples of quaternary ammonium salts include:

quaternary ammonium salts of formula (IV) below:

in which:
the radicals $R_1$, $R_2$, $R_3$, and $R_4$, which may be identical or different, are independently chosen from linear and branched aliphatic radicals comprising from 1 to 30 carbon atoms, and aromatic radicals, such as $C_6$–$C_{20}$ aromatic radicals (for example, aryl and alkylaryl), wherein the aliphatic radicals can comprise at least one atom chosen from halogen atoms and hetero atoms, such as, oxygen, nitrogen, and sulfur, and wherein the aliphatic radicals are chosen, for example, from alkyl, alkoxy, polyoxy($C_2$–$C_6$) alkylene, alkylamide, ($C_{12}$–$C_{22}$)alkylamido($C_2$–$C_6$) alkyl, ($C_{12}$–$C_{22}$)alkylacetate and hydroxyalkyl radicals, comprising from 1 to 30 carbon atoms;
X is an anion chosen from halides, phosphates, anions derived from organic acids, ($C_2$–$C_6$)alkyl sulfates, alkyl sulfonates, and alkylaryl sulfonates.

Quaternary ammonium salts of imidazolinium of formula (V) below:

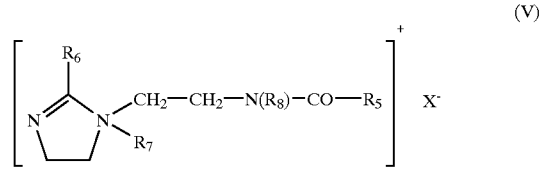

in which:
$R_5$ is chosen from alkenyl and alkyl radicals comprising from 8 to 30 carbon atoms, for example radicals derived from tallow fatty acid,
$R_6$ is chosen from a hydrogen atom, $C_1$–$C_4$ alkyl radicals, and alkenyl and alkyl radicals comprising from 8 to 30 carbon atoms,
$R_7$ is chosen from $C_1$–$C_4$ alkyl radicals,
$R_8$ is chosen from a hydrogen atom and $C_1$–$C_4$ alkyl radicals,
X⁻ is an anion chosen from halides, phosphates, acetates, lactates, alkyl sulfates, alkyl sulfonates, and alkylaryl sulfonates.

For example, $R_5$ and $R_6$, which may be identical or different, are independently chosen from alkenyl and alkyl radicals comprising from 12 to 21 carbon atoms, for example, radicals derived from tallow fatty acid, $R_7$ is methyl, and $R_8$ is hydrogen.

Such a products is sold, for example, under the name "Rewoquat" W 75" by Rewo.

Diquaternary ammonium salts of formula (VI):

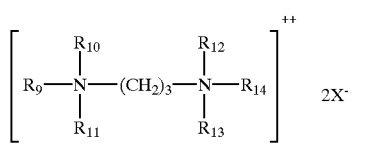

in which:

$R_9$ is chosen from aliphatic radicals comprising from 16 to 30 carbon atoms, $R_{10}$, $R_{11}$, $R_{12}$, $R_{13}$ and $R_{14}$, which may be identical or different, are independently chosen from a hydrogen atom and alkyl radicals comprising from 1 to 4 carbon atoms, and $X^-$ is an anion chosen from halides, acetates, phosphates, nitrates and methyl sulfates.

For example, such diquaternary ammonium salts can comprise propane tallow diammonium dichloride.

Quaternary ammonium salts of formula (VII) below comprising at least one ester function:

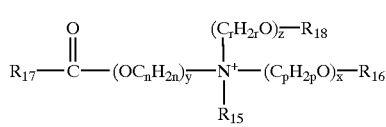

in which:

$R_{15}$ is chosen from $C_1$–$C_6$ alkyl radicals and $C_1$–$C_6$ hydroxyalkyl and $C_1$–$C_6$ dihydroxyalkyl radicals;

$R_{16}$ is chosen from:

acyl groups of the following formula:

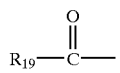

wherein $R_{19}$ is defined below, linear and branched, saturated and unsatruated, $C_1$–$C_{22}$ hydrocrbon-based radicals, and a hydrogen atom;

$R_{18}$ is chosen from:

acyl groups of the following formula;

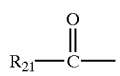

wherein $R_{21}$ is defined below, linear and branched, saturated and unsaturated, $C_1$–$C_6$ hydrocarbon-based radicals, and a hydrogen atom;

$R_{17}$, $R_{19}$ and $R_{21}$, which may be identical or different, are independently chosen from linear and branched, saturated and unsaturated, $C_7$–$C_{21}$ hydrocarbon-based radicals;

n, p and r, which may be identical or different, are independently integers ranging from 2 to 6;

y is an integer ranging from 1 to 10;

x and z, which may be identical or different, are independently integers ranging from 0 to 10;

$X^-$ is chosen from simple and complex, organic and inorganic anions;

provided that the sum x+y+z is from 1 to 15, and that when x is 0, then $R_{16}$ is chosen from linear and branched, saturated and unsaturated, $C_1$–$C_{22}$ hydrocarbon-based radicals, and that when z is 0, then $R_{18}$ is chosen from linear and branched, saturated and unsaturated, $C_1$–$C_6$ hydrocarbon-based radicals.

In one embodiment, the $R_{15}$ alkyl radicals may be linear and branched, such as, for example, linear.

For example, $R_{15}$ may be chosen from methyl, ethyl, hydroxyethyl and dihydroxypropyl radicals, such as, for example, from methyl and ethyl radicals.

The sum x+y+z may for example range from 1 to 10.

When $R_{16}$ is chosen from linear and branched, saturated and unsaturated, $C_1$–$C_{22}$ hydrocarbon-based radicals, $R_{16}$ may be long and comprise from 12 to 22 carbon atoms, or short and comprise from 1 to 3 carbon atoms.

When $R_{18}$ is chosen from linear and branched, saturated and unsaturated, $C_1$–$C_6$ hydrocarbon-based radicals, $R_{18}$ may for example comprise from 1 to 3 carbon atoms.

$R_{17}$, $R_{19}$ and $R_{21}$, which may be identical or different, can, for example, be independently chosen from linear and branched, saturated and unsaturated $C_{11}$–$C_{21}$ hydrocarbon-based radicals, such as, for example, from linear and branched, saturated and unsaturated, $C_{11}$–$C_{21}$ alkyl and alkenyl radicals.

x and z, which may be identical or different, can for example independently be chosen from 0 or 1.

y for example may be equal to 1.

n, p and r, which may be identical or different, can for example be independently chosen from 2 and 3 and in one embodiment equal to 2.

The anion for example can be chosen from halides (chloride, bromide, and iodide) and alkyl sulfates, such as methyl sulfate. However, methanesulfonate, phosphate, nitrate, tosylate, anions derived from organic acids, such as acetate and lactate, and any other anions compatible with the ammonium comprising an ester function, may also be used.

As a further example, the anion $X^-$ can be chosen from chloride and methyl sulfate.

Further examples of ammonium salts of formula (VII) are those in which:

$R_{15}$ is chosen from methyl and ethyl radicals, x and y are equal to 1;

z is equal to 0 or 1;

n, p and r are equal to 2;

$R_{16}$ is chosen from:

wherein $R_{19}$ is defined below, methyl, ethyl and $C_{14}$–$C_{22}$ hydrocarbon-based radicals, and a hydrogen atom;

$R_{18}$ is chosen from:

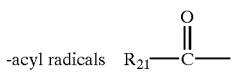
-acyl radicals $R_{21}-\overset{\overset{O}{\|}}{C}-$ wherein $R_{21}$ is defined below,
a hydrogen atom;
$R_{17}$, $R_{19}$ and $R_{21}$, which may be identical or different, are independently chosen from linear and branched, saturated and unsaturated, $C_{13}$–$C_{17}$ hydrocarbon-based radicals, such as from linear and branched, saturated and unsaturated $C_{13}$–$C_{17}$ alkyl and alkenyl radicals.

The hydrocarbon-based radicals can for example be linear.

Representative compounds of formula (VII) are chosen from diacyloxyethyl-dimethylammonium, diacyloxyethylhydroxyethylmethylammonium, monoacyloxyethyldihydroxyethylmethylammonium, triacyloxyethyl methylammonium and monoacyloxyethylhydroxyethyldimethylammonium salts (for example chloride and methyl sulfate). The acyl radicals can for example comprise from 14 to 18 carbon atoms and can for example be obtained from vegetable oils, such as palm oil and sunflower oil. When the compound comprises several acyl radicals, these radicals, which may be independently chosen, may independently be identical or different.

These products are obtained, for example, by direct esterification of compounds chosen from triethanolamine, triisopropanolamine, alkyldiethanolamines and alkyldiisopropanolamines, which are optionally oxyalkylenated, with fatty acids or with fatty acid mixtures of vegetable or animal origin, and by transesterification of the methyl esters thereof. This esterification is followed by a quaternization using an alkylating agent such as alkyl halides (such ad methyl and ethyl halides), dialkyl sulfates (for example dimethyl and diethyl sulfates), methyl methanesulfonate, methyl para-toluenesulfonate, glycol chlorohydrin and glycerol chlorohydrin.

Such compounds are sold, for example, under the names Dehyquart by the company Henkel, Stepanquat by the company Stepan, Noxamium by the company Ceca and Rewoquat WE 18 by the company Rewo-Witco.

It is also possible to use the ammonium salts comprising at least one ester function, described in patents U.S. Pat. No. 4,874,554 and U.S. Pat. No. 4,137,180, the disclosures of which are incorporated by reference herein.

Representative quaternary ammonium salts of formula (IV) include tetraalkylammonium chlorides such as, for example, dialkyldimethylammonium chlorides and alkyltrimethylammonium chlorides, in which the alkyl radical comprises from 12 to 22 carbon atoms, for example behenyltrimethylammonium chloride, distearyldimethylammonium chloride, cetyltrimethylammonium chloride, and benzyldimethylstearylammonium chloride, and, stearamidopropyldimethyl(myristyl acetate)ammonium chloride sold under the name "Cepharyl 70" by the company Van Dyk.

The fatty alcohols may be chosen from linear and branched $C_8$–$C_{22}$ fatty alcohols; they may be optionally oxyalkylenated with 1 to 15 mol of alkylene oxide. They may also be optionally polyglycerolated with 1 to 6 mol of glycerol. The alkylene oxide may, for example, be chosen from ethylene oxide and propylene oxide.

For example, the fatty alcohols may be chosen from lauryl alcohol, myristyl alcohol, cetyl alcohol, stearyl alcohol, oleyl alcohol, isostearyl alcohol, isocetyl alcohol, oleyl alcohol, and lauryl alcohols oxyethylenated with 2 to 8 mol of ethylene oxide.

The fatty acids may, for example, be chosen from myristic acid, palmitic acid, stearic acid, behenic acid, oleic acid, linoleic acid, linolenic acid, and isostearic acid.

The derivatives of fatty alcohols and the derivatives of fatty acids may be, for example, the esters of carboxylic acids, such as, for example, the mono-, di-, tri- and tetra-carboxylic esters.

The esters of monocarboxylic acids can be, for example, the monoesters of saturated and unsaturated, linear and branched, $C_1$–$C_{26}$ aliphatic acids and of saturated and unsaturated, linear and branched, $C_1$–$C_{26}$ aliphatic alcohols, the total carbon number of the esters being greater than or equal to 10.

Mention may be made, among the monoesters, of dihydroabietyl behenate, octyldodecyl behenate, isocetyl behenate, cetyl lactate, $C_{12}$–$C_{15}$ alkyl lactate, isostearyl lactate, lauryl lactate, linoleyl lactate, oleyl lactate, (iso)stearyl octanoate, isocetyl octanoate, octyl octanoate, cetyl octanoate, decyl oleate, isocetyl isostearate, isocetyl laurate, isocetyl stearate, isodecyl octanoate, isodecyl oleate, isononyl isononanoate, isostearyl palmitate, methyl acetylricinoleate, myristyl stearate, octyl isononanoate, 2-ethylhexyl isononanoate, octyl palmitate, octyl pelargonate, octyl stearate, octyldodecyl erucate, oleyl erucate, ethyl palmitate, isopropyl palmitate, 2-ethylhexyl palmitate, 2-octyldecyl palmitate, alkyl myristates, such as isopropyl myristate, butyl myristate, cetyl myristate, and 2-octyldodecyl myristate, hexyl stearate, butyl stearate, isobutyl stearate, dioctyl malate, hexyl laurate, and 2-hexyldecyl laurate.

Use may also be made of esters of $C_4$–$C_{22}$ dicarboxylic and $C_4$–$C_{22}$ tricarboxylic acids and of $C_1$–$C_{22}$ alcohols and esters of mono-, di- and tricarboxylic acids and of $C_2$–$C_{26}$ di-, tri-, tetra-, and pentahydroxy alcohols.

Mention may, for example, be made of: diethyl sebacate, diisopropyl sebacate, diisopropyl adipate, di(n-propyl) adipate, dioctyl adipate, diisostearyl adipate, dioctyl maleate, glyceryl undecylenate, stearoyloctyidodecyl stearate, pentaerythrityl monoricinoleate, pentaerythrityl tetraisononanoate, pentaerythrityl tetrapelargonate, pentaerythrityl tetraisostearate, pentaerythrityl tetraoctanoate, propylene glycol dicaprylate/dicaprate, tridecyl erucate, triisopropyl citrate, triisostearyl citrate, glyceryl trilactate, glyceryl trioctanoate, trioctyidodecyl citrate, and trioleyl citrate.

Use, for example, may be made, among the abovementioned esters, of ethyl and isopropyl palmitates; 2-ethylhexyl palmitate; 2-octyldecyl palmitate; alkyl myristates, such as isopropyl, butyl, cetyl and 2-octyidodecyl myristate; hexyl stearate; butyl stearate; isobutyl stearate; dioctyl malate; hexyl laurate; 2-hexyldecyl laurate; isononyl isononanoate and cetyl octanoate.

The fluorinated oils may be, for example, the perfluoropolyethers disclosed, for example, in Patent Application EP-A-486,135 and the fluorohydrocarbon compounds disclosed, for example, in Patent Application WO 93/11103, the disclosures of which are incorporated herein by reference.

The term "fluorohydrocarbon compounds" denotes compounds with a chemical structure comprising a carbon backbone, wherein at least one hydrogen atom has been substituted by at least one fluorine atom.

The fluorinated oils may also be fluorocarbons, such as fluoroamines, for example perfluorotributylamine, fluorinated hydrocarbons, for example perfluorodecahydronaphthalene, fluoroesters and fluoroethers.

The perfluoropolyethers are, for example, sold under the trade names Fomblin by Montefluos and Krytox by Du Pont.

Mention may also be made, among the fluorohydrocarbon compounds, of fluorinated fatty acid esters, such as, for example, the product sold under the name Nofable FO by Nippon Oil.

According to the invention, the at least one beneficial agent may be present, for example, in an amount generally ranging from 0.01% to 15% by weight, such as from 0.05% to 10% by weight, relative to the total weight of the final composition.

The cosmetically acceptable medium may comprise at least one component chosen from water and at least one cosmetically acceptable solvent. Non-limiting examples of cosmetically acceptable solvents include alcohols and volatile cyclic silicones. For example, cosmetically acceptable solvents may be $C_1$–$C_4$ alcohols.

At least one nonaqueous solvent may be present, for example, in an amount generally ranging from up to 99.9%, such as from up to 60% by weight, relative to the total weight of the composition.

The composition according to the invention may also comprise at least one thickening agent, such as, for example, at least one polymeric thickening agent.

Within the meaning of the present invention, the term "thickening agent" is understood to mean any agent capable of increasing the viscosity of a cosmetic composition.

The at least one thickening agent may chosen from natural thickening agents and synthetic thickening agents. Non-limiting examples of natural thickening agents include xanthan gum, scleroglucan gum, gellan gum, rhamsan gum, alginates, maltodextrin, starch, derivatives of starch, karaya gum, locus bean flour; guar gums, celluloses, and derivatives of celluloses.

Non-limiting examples of synthetic thickening agents include polymers of acrylic acid, polymers of methacrylic acid, and copolymers of acrylic acid and methacrylic acid, such as acrylic acid/ethyl acrylate copolymers and carboxyvinyl polymers. Examples of such polymers and copolymers include the "carbomers" (CTFA) sold by Goodrich under the name Carbopol, such as Carbopol Ultrez 10, the polyglyceryl methacrylate sold by Guardian under the name Lubragel, and the polyglyceryl acrylate sold under the name Hispagel by Hispano Chimica. Carbopol Ultrez 10 is a member of a class called Carbomer, the class being defined as a homopolymer of acrylic acid crosslinked with an allyl ether of pentaerythritol, an allyl ether of sucrose, or an allyl ether of propylene. See International Cosmetic Ingredient Dictionary and Handbook, Seventh Edition, 1997, Volume 1, page 204, the disclosure of which is incorporated by reference herein.

Mention may be made, for example, of acrylic and methacrylic acid copolymers comprising at least one unit chosen from $C_1$ to $C_{30}$ alkyl acrylate units and urethane units optionally substituted by a fatty chain. Mention may be made, for example, of Pemulen TR1 (Goodrich), Viscophobe DB 1000 (Union Carbide), and Acrysol 44 and Acrysol 46 (Rohm & Haas).

Use may also be made for example, as thickening agents, of polyethylene glycols (PEG) and polyethylene glycol derivatives.

Use may also be made for example, as thickening agents, of thickening polyacrylamides. The latter can, for example, be chosen from:

crosslinked homopolymers of 2-acrylamido-2-methylpropanesulfonic acid;

optionally crosslinked copolymers of acrylamide and of ammonium acrylate;

optionally crosslinked copolymers of acrylamide, methacrylamide, and methacryloyloxyethyltrimethylammonium chloride; and partially and completely neutralized and optionally crosslinked copolymers of acrylamide and of 2-acrylamido-2-methylpropanesulfonic acid.

Mention may be made for example, as crosslinked copolymers of acrylamide/ammonium acrylate used in accordance with the present invention, of acrylamide/ammonium acrylate (5/95 by weight) copolymers crosslinked by at least one crosslinking agent with more than one olefinic unsaturation, such as divinylbenzene, tetraallyloxyethane, methylenebisacrylamide, diallyl ether, polyallylpolyglyceryl ethers and allyl ethers of an alcohol from the series of the sugars, such as erythritol, pentaerythritol, arabitol, mannitol, sorbitol and glucose.

Analogous copolymers are disclosed and prepared in French Patent FR-2,416,723 and Patents U.S. Pat. No. 2,798,053 and U.S. Pat. No. 2,923,692, the disclosures of which are incorporated herein by reference.

This type of crosslinked copolymer is used, for example, in the form of a water-in-oil emulsion comprising approximately: 30% by weight of the said crosslinked copolymer, 25% by weight of liquid paraffin, 4% by weight of a mixture of sorbitan stearate and a hydrophilic ethoxylated derivative, and 41% by weight of water. Such an emulsion is, for example, sold under the name "Bozepol C" by Hoechst.

The copolymers of acrylamide and of 2-acrylamido-2-methylpropanesulfonic acid used in accordance with the present invention are copolymers which are crosslinked by at least one compound with more than one olefinic unsaturation, such as those mentioned above, and which are partially or completely neutralized by at least one neutralizing agent, such as, for example, an agent chosen from sodium hydroxide, potassium hydroxide, aqueous ammonia and an amine, such as triethanolamine and monoethanolamine.

They can, for example, be prepared by copolymerizing acrylamide and sodium 2-acrylamido-2-methylpropanesulfonate by the radical route by means of at least one initiating agent of the azobisisobutyronitrile type and by precipitation from at least one alcohol, such as tert-butanol.

Use, for example, may be made of copolymers obtained by copolymerization of acrylamide, generally ranging from 70% to 55 mol %; and sodium 2-acrylamido-2-methylpropanesulfonate, generally ranging from 30% to 45 mol %; wherein the at least one crosslinking agent is used at concentrations generally ranging from $10^{-4}$ to $4\times10^-$-mol per mole of the mixture of monomers.

These copolymers may be incorporated in the compositions of the invention, for example, in the form of water-in-oil emulsions comprising: said copolymer, in an amount generally ranging from 35% to 40% by weight; a mixture of $C_{12}$-$C_{13}$ isoparaffin hydrocarbons, in an amount generally ranging from 15% to 25% by weight; polyethylene glycol lauryl ether comprising 7 mol of ethylene oxide, in an amount generally ranging from 3% to 8% by weight; and water.

According to the invention it is also possible to use at least one hair dye. The at least one hair dye may, for example, be chosen from inorganic and organic pigments; soluble direct dyes belonging to the following classes: nitro, azo, quinone (anthraquinone, naphthoquinone, benzoquinone), xanthene, triarylmethane and indoamine; and oxidation dyes (oxidation base, such as para-phenylenediamines, paraiminophenols, orthoaminophenols and heterocyclic bases, optionally used in combination with a coupler, such as meta-phenylenediamines, meta-aminophenols, meta-diphenols, naphthols, and heterocyclic couplers).

The composition of the invention may also comprise at least one additive chosen from anionic, nonionic, and amphoteric surfactants; polyols, such as glycol and glycerol; pigments; dyes; fragrances; screening agents; preservatives; proteins; vitamins; provitamins; polymers other than those of the invention and any other additive conventionally used in cosmetic compositions.

The roll-on applicators according to the invention may be used, for example, to deposit on the hair, at least one composition chosen from care compositions; compositions for fixing and for retaining the form of the hairstyle; conditioners; and hair balms.

Of course, a person skilled in the art will take care to choose the possible compound(s) to be added to the composition according to the invention so that at least one advantageous property intrinsically associated with the composition in accordance with the invention is not, or not substantially, detrimentally affected by the envisaged addition.

The invention will be further illustrated with the help of the following non-limiting examples.

All the percentages are relative percentages by weight with respect to the total weight of the composition; a.m. means active material.

The constituents used in Examples 1 through 6 are collated in the table below.

| | |
|---|---|
| Synthalen K | Acrylic polymer, sold by 3V |
| Mirasil DMCO | Dimethicone copolyol, sold by Rhône-Poulenc (now Rhodia) |
| Jaguar HP 105 | Hydroxypropyl gum, sold by Rhône-Poulenc (now Rhodia |
| Arquad 16-25 LO | Cetrimonium chloride, sold by Akzo Nobel |
| Gafquat 734 | Polyquaternium-11, sold by ISP |
| Celquat LOR | Polyquaternium-4, sold by National Starch |
| Solanace Starch | Modified potato starch, sold by National Starch |
| Ultrez 10 | Carbomer, sold by Goodrich |
| Luvimer MAE | Acrylate copolymer, sold by BASF |
| DC x and DCx fluid | Silicone, sold by Dow Corning |
| Genamin | Behenalkonium chloride, sold by Hoechst |
| Aristoflex A | Vinyl acetate/crotonic acid/polyethylene glycol copolymer as a 60% solution in an IPA 87.4/water 12.6 mixture |
| Polyethylene glycol 400 | Ethylene oxide polymer, sold by Dow Chemical |
| Abil B8842 | Cetyldimethicone copolyol, sold by Goldschmidt |
| Aculyn 22 | Acrylate/methacrylate copolymer, sold by Rohm & Haas |
| Ultrez 10 | Acrylic polymer, sold by Goodrich |
| Jaguar HP 105 | Gum, sold by Rhône-Poulenc (now Rhodia) |
| Ultrahold Strong | Acrylate copolymer, sold by BASF |

EXAMPLES

Roll-on applicators according to the invention were manufactured comprising various cosmetic compositions A to H forming the object of Examples 1 to 6 below.

Example 1

| | A | B |
|---|---|---|
| Synthalen K | 0.5 | 1 |
| Aristoflex A | 3% a.m. | |
| Mirasil DMCO | 0.1 | |
| Fragrance | 0.3 | |
| Ethanol | 40 | |
| AMP | q.s. for pH 7.6 | |
| Water | q.s. for 100 | |

Example 2

| | C |
|---|---|
| Jaguar HP 105 | 0.5 |
| Glycerol | 0.5 |
| Arquad 16-25 LO | 2 |
| Mirasil DMCO | 0.5 |
| PVP | 2 |
| Gafquat 734 | 0.2 |
| Celquat LOR | 0.2 |
| Perfume | 0.15 |
| Ethanol | 35 |
| AMP | q.s. for pH 7.2 |
| Water | q.s. for 100 |

Example 3

| | D |
|---|---|
| Solanace Starch | 0.25 |
| Ultrez 10 | 0.4 |
| Luvimer MAE | 6.6 |
| Celquat LOR | 0.3 |
| DC 2-1182 | 3 |
| Genamin | 0.45 |
| DC 939 | 0.5 |
| Propylene glycol | 2.5 |
| Preservatives | 0.7 |
| Perfume | q.s. for pH 7.2 |
| Water | q.s. for 100 |

Example 4

| | E | F |
|---|---|---|
| DC 556 fluid | 15 | |
| DC 200 fluid | 25 | 30 |
| Fragrance | 0.15 | |
| Ethanol | 5 | |
| DC 245 fluid | q.s. for 100 | |

Example 5

| | G |
|---|---|
| Aristoflex A | 5 (3% a.m.) |
| Glycerol | 11 |
| Polyethylene glycol 400 | 2.2 |
| Abil B8842 | 1.7 |
| Aculyn 22 | 1.7 |
| Fragrance | 0.2 |
| Preservatives | 0.7 |
| Triethanolamine | q.s. for pH 8 |
| Water | q.s. for 100 |

Example 6

| | H |
|---|---|
| Ultrez 10 | 0.3 |
| Luvimer MAE | 6.6 |
| Jaguar HP105 | 0.05 |
| Ultrahold Strong | 0.5 |
| DC 556 fluid | 20 |
| DC 245 fluid | 22 |

| | |
|---|---|
| AMP | q.s. for pH 7.5 |
| Water | q.s. for 100 |

The compositions A to H in accordance with the invention, forming the object of Examples 1 to 6, were introduced into the ball device sold by Weener Plastic under the designation "Ball and ball carrier assembly for roll-on". The compositions were applied to the hair. As a finishing application, the direct application made it possible to act over the whole of the hair and to carry out localized retouching.

According to the type of product used, hairstyles were obtained for which the locks:

- were better controlled with more body and styling,
- gave the impression of being slightly wet (a wet effect),
- had more softness and ease of disentangling,
- had a pronounced sheen.

The constituents recited in prophetic Examples 7 through 51 are collated in the table below.

| | |
|---|---|
| Resin 28-29-30 | crotonic acid/vinyl acetate/vinyl neododecanoate terpolymer, sold by National Starch |
| Gantrez ES 425 | monoesterified methyl vinyl ether/maleic anyhdride copolymer, sold by ISP |
| Aristoflex A | vinyl acetate/crotonic acid copolymer grafted by polyethylene glycol, sold by Clariant |
| EX-SDR26 | vinyl acetate/crotonic acid copolymer, provided by Goodrich |
| Eudragit L | methacrylic acid/methyl methacrylate copolymer, sold by Rohm Pharma |
| Lubragel | polyglyceryl methacrylate, sold by Guardian |
| Carbopol Ultrez 10 | "carbomer" (CTFA), sold by Goodrich |
| Hispagel | polyglyceryl acrylate, sold by Hispano Chimica |
| 70,047 V 500,000 | silbione oil, sold by Rhodia |
| Mirasil DMCO-oil 70,646 | oil of the Mirasil series, sold by Rhodia |
| Dow Corning 190 Surfactant | surfactant, sold by Dow Corning |

In Examples 7–51, the composition is in the form of a hair fixing gel in a water and alcohol solvent medium. "Classical additives" means at least one additive chosen from preservatives and perfumes.

Example 7

| | |
|---|---|
| Resin 28-29-30 | 1–3 |
| Lubragel | 0.5–1 |
| Mirasil DMCO-oil 70,646 | 0.1–0.2 |
| alcohol | 5–30 |
| classical additives | q.s. |
| water | q.s. for 100 |

Example 8

| | |
|---|---|
| Gantrez ES 425 | 1–3 |
| Lubragel | 0.5–1 |
| Mirasil DMCO-oil 70,646 | 0.1–0.2 |
| alcohol | 5–30 |
| classical additives | q.s. |
| water | q.s. for 100 |

Example 9

| | |
|---|---|
| Aristoflex A | 1–3 |
| Lubragel | 0.5–1 |
| Mirasil DMCO-oil 70,646 | 0.1–0.2 |
| alcohol | 5–30 |
| classical additives | q.s. |
| water | q.s. for 100 |

Example 10

| | |
|---|---|
| Eudragit L | 1–3 |
| Lubragel | 0.5–1 |
| Mirasil DMCO-oil 70,646 | 0.1–0.2 |
| alcohol | 5–30 |
| classical additives | q.s. |
| water | q.s. for 100 |

Example 11

| | |
|---|---|
| EX-SDR26 | 1–3 |
| Lubragel | 0.5–1 |
| Mirasil DMCO-oil 70,646 | 0.1–0.2 |
| alcohol | 5–30 |
| classical additives | q.s. |
| water | q.s. for 100 |

Example 12

| | |
|---|---|
| Resin 28-29-30 | 1–3 |
| Carbopol Ultrez 10 | 0.5–1 |
| Mirasil DMCO-oil 70,646 | 0.1–0.2 |
| alcohol | 5–30 |
| classical additives | q.s. |
| water | q.s. for 100 |

Example 13

| | |
|---|---|
| Gantrez ES 425 | 1–3 |
| Carbopol Ultrez 10 | 0.5–1 |
| Mirasil DMCO-oil 70,646 | 0.1–0.2 |
| alcohol | 5–30 |
| classical additives | q.s. |
| water | q.s. for 100 |

Example 14

| | |
|---|---|
| Aristoflex A | 1–3 |
| Carbopol Ultrez 10 | 0.5–1 |
| Mirasil DMCO-oil 70,646 | 0.1–0.2 |
| alcohol | 5–30 |
| classical additives | q.s. |
| water | q.s. for 100 |

Example 15

| | |
|---|---|
| Eudragit L | 1–3 |
| Carbopol Ultrez 10 | 0.5–1 |
| Mirasil DMCO-oil 70,646 | 0.1–0.2 |
| alcohol | 5–30 |
| classical additives | q.s. |
| water | q.s. for 100 |

Example 16

| | |
|---|---|
| EX-SDR26 | 1–3 |
| Carbopol Ultrez 10 | 0.5–1 |
| Mirasil DMCO-oil 70,646 | 0.1–0.2 |
| alcohol | 5–30 |
| classical additives | q.s. |
| water | q.s. for 100 |

Example 17

| | |
|---|---|
| Resin 28-29-30 | 1–3 |
| Hispagel | 0.5–1 |
| Mirasil DMCO-oil 70,646 | 0.1–0.2 |
| alcohol | 5–30 |
| classical additives | q.s. |
| water | q.s. for 100 |

Example 18

| | |
|---|---|
| Gantrez ES 425 | 1–3 |
| Hispagel | 0.5–1 |
| Mirasil DMCO-oil 70,646 | 0.1–0.2 |
| alcohol | 5–30 |
| classical additives | q.s. |
| water | q.s. for 100 |

Example 19

| | |
|---|---|
| Aristoflex A | 1–3 |
| Hispagel | 0.5–1 |
| Mirasil DMCO-oil 70,646 | 0.1–0.2 |

-continued

| | |
|---|---|
| alcohol | 5–30 |
| classical additives | q.s. |
| water | q.s. for 100 |

Example 20

| | |
|---|---|
| Eudragit L | 1–3 |
| Hispagel | 0.5–1 |
| Mirasil DMCO-oil 70,646 | 0.1–0.2 |
| alcohol | 5–30 |
| classical additives | q.s. |
| water | q.s. for 100 |

Example 21

| | |
|---|---|
| EX-SDR26 | 1–3 |
| Hispagel | 0.5–1 |
| Mirasil DMCO-oil 70,646 | 0.1–0.2 |
| alcohol | 5–30 |
| classical additives | q.s. |
| water | q.s. for 100 |

Example 22

| | |
|---|---|
| Resin 28-29-30 | 1–3 |
| Lubragel | 0.5–1 |
| 70,047 V 500,000 | 0.1–0.2 |
| alcohol | 5–30 |
| classical additives | q.s. |
| water | q.s. for 100 |

Example 23

| | |
|---|---|
| Gantrez ES 425 | 1–3 |
| Lubragel | 0.5–1 |
| 70,047 V 500,000 | 0.1–0.2 |
| alcohol | 5–30 |
| classical additives | q.s. |
| water | q.s. for 100 |

Example 24

| | |
|---|---|
| Aristoflex A | 1–3 |
| Lubragel | 0.5–1 |
| 70,047 V 500,000 | 0.1–0.2 |
| alcohol | 5–30 |
| classical additives | q.s. |
| water | q.s. for 100 |

Example 25

| | |
|---|---|
| Eudragit L | 1–3 |
| Lubragel | 0.5–1 |
| 70,047 V 500,000 | 0.1–0.2 |
| alcohol | 5–30 |
| classical additives | q.s. |
| water | q.s. for 100 |

Example 26

| | |
|---|---|
| EX-SDR26 | 1–3 |
| Lubragel | 0.5–1 |
| 70,047 V 500,000 | 0.1–0.2 |
| alcohol | 5–30 |
| classical additives | q.s. |
| water | q.s. for 100 |

Example 27

| | |
|---|---|
| Resin 28-29-30 | 1–3 |
| Carbopol Ultrez 10 | 0.5–1 |
| 70,047 V 500,000 | 0.1–0.2 |
| alcohol | 5–30 |
| classical additives | q.s. |
| water | q.s. for 100 |

Example 28

| | |
|---|---|
| Gantrez ES 425 | 1–3 |
| Carbopol Ultrez 10 | 0.5–1 |
| 70,047 V 500,000 | 0.1–0.2 |
| alcohol | 5–30 |
| classical additives | q.s. |
| water | q.s. for 100 |

Example 29

| | |
|---|---|
| Aristoflex A | 1–3 |
| Carbopol Ultrez 10 | 0.5–1 |

-continued

| | |
|---|---|
| 70,047 V 500,000 | 0.1–0.2 |
| alcohol | 5–30 |
| classical additives | q.s. |
| water | q.s. for 100 |

Example 30

| | |
|---|---|
| Eudragit L | 1–3 |
| Carbopol Ultrez 10 | 0.5–1 |
| 70,047 V 500,000 | 0.1–0.2 |
| alcohol | 5–30 |
| classical additives | q.s. |
| water | q.s. for 100 |

Example 31

| | |
|---|---|
| EX-SDR26 | 1–3 |
| Carbopol Ultrez 10 | 0.5–1 |
| 70,047 V 500,000 | 0.1–0.2 |
| alcohol | 5–30 |
| classical additives | q.s. |
| water | q.s. for 100 |

Example 32

| | |
|---|---|
| Resin 28-29-30 | 1–3 |
| Hispagel | 0.5–1 |
| 70,047 V 500,000 | 0.1–0.2 |
| alcohol | 5–30 |
| classical additives | q.s. |
| water | q.s. for 100 |

Example 33

| | |
|---|---|
| Gantrez ES 425 | 1–3 |
| Hispagel | 0.5–1 |
| 70,047 V 500,000 | 0.1–0.2 |
| alcohol | 5–30 |
| classical additives | q.s. |
| water | q.s. for 100 |

Example 34

| | |
|---|---|
| Aristoflex A | 1–3 |
| Hispagel | 0.5–1 |
| 70,047 V 500,000 | 0.1–0.2 |
| alcohol | 5–30 |
| classical additives | q.s. |
| water | q.s. for 100 |

Example 35

| | |
|---|---|
| Eudragit L | 1–3 |
| Hispagel | 0.5–1 |
| 70,047 V 500,000 | 0.1–0.2 |
| alcohol | 5–30 |
| classical additives | q.s. |
| water | q.s. for 100 |

Example 36

| | |
|---|---|
| EX-SDR26 | 1–3 |
| Hispagel | 0.5–1 |
| 70,047 V 500,000 | 0.1–0.2 |
| alcohol | 5–30 |
| classical additives | q.s. |
| water | q.s. for 100 |

Example 37

| | |
|---|---|
| Resin 28-29-30 | 1–3 |
| Lubragel | 0.5–1 |
| Dow Corning 190 Surfactant | 0.1–0.2 |
| alcohol | 5–30 |
| classical additives | q.s. |
| water | q.s. for 100 |

Example 38

| | |
|---|---|
| Gantrez ES 425 | 1–3 |
| Lubragel | 0.5–1 |
| Dow Corning 190 Surfactant | 0.1–0.2 |
| alcohol | 5–30 |
| classical additives | q.s. |
| water | q.s. for 100 |

Example 39

| | |
|---|---|
| Aristoflex A | 1–3 |

| | |
|---|---|
| *-continued* | |
| Lubragel | 0.5–1 |
| Dow Corning 190 Surfactant | 0.1–0.2 |
| alcohol | 5–30 |
| classical additives | q.s. |
| water | q.s. for 100 |
| *Example 40* | |
| Eudragit L | 1–3 |
| Lubragel | 0.5–1 |
| Dow Corning 190 Surfactant | 0.1–0.2 |
| alcohol | 5–30 |
| classical additives | q.s. |
| water | q.s. for 100 |
| *Example 41* | |
| EX-SDR26 | 1–3 |
| Lubragel | 0.5–1 |
| Dow Corning 190 Surfactant | 0.1–0.2 |
| alcohol | 5–30 |
| classical additives | q.s. |
| water | q.s. for 100 |
| *Example 42* | |
| Resin 28-29-30 | 1–3 |
| Carbopol Ultrez 10 | 0.5–1 |
| Dow Corning 190 Surfactant | 0.1–0.2 |
| alcohol | 5–30 |
| classical additives | q.s. |
| water | q.s. for 100 |
| *Example 43* | |
| Gantrez ES 425 | 1–3 |
| Carbopol Ultrez 10 | 0.5–1 |
| Dow Corning 190 Surfactant | 0.1–0.2 |
| alcohol | 5–30 |
| classical additives | q.s. |
| water | q.s. for 100 |
| *Example 44* | |
| Aristoflex A | 1–3 |
| Carbopol Ultrez 10 | 0.5–1 |
| Dow Corning 190 Surfactant | 0.1–0.2 |
| alcohol | 5–30 |
| classical additives | q.s. |
| water | q.s. for 100 |
| *Example 45* | |
| Eudragit L | 1–3 |
| Carbopol Ultrez 10 | 0.5–1 |
| Dow Corning 190 Surfactant | 0.1–0.2 |
| alcohol | 5–30 |
| classical additives | q.s. |
| water | q.s. for 100 |
| *Example 46* | |
| EX-SDR26 | 1–3 |
| Carbopol Ultrez 10 | 0.5–1 |
| Dow Corning 190 Surfactant | 0.1–0.2 |
| alcohol | 5–30 |
| classical additives | q.s. |
| water | q.s. for 100 |
| *Example 47* | |
| Resin 28-29-30 | 1–3 |
| Hispagel | 0.5–1 |
| Dow Corning 190 Surfactant | 0.1–0.2 |
| alcohol | 5–30 |
| classical additives | q.s. |
| water | q.s. for 100 |
| *Example 48* | |
| Gantrez ES 425 | 1–3 |
| Hispagel | 0.5–1 |
| Dow Corning 190 Surfactant | 0.1–0.2 |
| alcohol | 5–30 |
| classical additives | q.s. |
| water | q.s. for 100 |

| | |
|---|---|
| *-continued* | |
| *Example 49* | |
| Aristoflex A | 1–3 |
| Hispagel | 0.5–1 |
| Dow Corning 190 Surfactant | 0.1–0.2 |
| alcohol | 5–30 |
| classical additives | q.s. |
| water | q.s. for 100 |
| *Example 50* | |
| Eudragit L | 1–3 |
| Hispagel | 0.5–1 |
| Dow Corning 190 Surfactant | 0.1–0.2 |
| alcohol | 5–30 |
| classical additives | q.s. |
| water | q.s. for 100 |
| *Example 51* | |
| EX-SDR26 | 1–3 |
| Hispagel | 0.5–1 |
| Dow Corning 190 Surfactant | 0.1–0.2 |
| alcohol | 5–30 |
| classical additives | q.s. |
| water | q.s. for 100 |

The compositions of Examples 7–51 may be used with the roll-on applicator sold by Weener Plastic under the designation "ball and ball carrier assembly for roll-on" (Narta type).

What is claimed is:

1. A roll-on applicator comprising a container and a rotatable application member on the container, the container containing a hair composition devoid of carboxylic surfactant, said hair composition comprising, in a cosmetically acceptable medium, at least one component chosen from:
    (i) anionic, amphoteric, and nonionic fixing polymers;
    (ii) beneficial agents; and
    (iii) hair dyes;
    wherein the roll-on applicator is capable of directly depositing on the hair said at least one component.

2. The roll-on applicator according to claim 1, wherein the at least one component is chosen from anionic, amphoteric, and nonionic fixing polymers; and beneficial agents.

3. The roll-on applicator according to claim 1, wherein the at least one component is chosen from anionic, amphoteric, and nonionic fixing polymers.

4. The roll-on applicator according to claim 3, wherein said at least one component is chosen from anionic fixing polymers chosen from:
    polymers comprising at least one carboxyl repeating unit derived from unsaturated mono- and dicarboxylic acid monomers of formula:

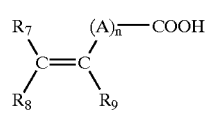

(II)

wherein:
    n is an integer ranging from 0 to 10,
    A is a methylene group, optionally connected to the carbon atom of the unsaturated group and, in addition, optionally connected to a neighboring methylene group when n is greater than 1 via a heteroatom,
    $R_7$ is chosen from hydrogen atoms, phenyl groups, and benzyl groups, $R_8$ is chosen from hydrogen atoms, lower alkyl groups, and carboxyl groups, and $R_9$ is chosen from hydrogen atoms, lower alkyl groups, —$CH_2$—COOH groups, phenyl groups, and benzyl groups; and polymers comprising at least one repeating unit derived from sulfonic acid.

5. The roll-on applicator according to claim 4, wherein the heteroatom is chosen from oxygen and sulfur.

6. The roll-on applicator according to claim 4, wherein the at least one repeating unit derived from sulfonic acid is chosen from vinylsulfonic units, styrenesulfonic units, and acrylamidoalkylsulfonic units.

7. The roll-on applicator according to claim 3, wherein said at least one component is chosen from amphoteric fixing polymers comprising at least one repeating unit derived from:
   a) monomers chosen from acrylamides substituted on the nitrogen with an alkyl radical and methacrylamides substituted on the nitrogen by an alkyl radical,
   b) acidic comonomers comprising at least one reactive carboxylic group, and
   c) basic comonomers.

8. The roll-on applicator according to claim 7, wherein the basic comonomers are selected from esters of acrylic acid and esters of methacrylic acid, said esters being substituted with at least one amine chosen from primary, secondary, tertiary, and quaternary amines, and quaternization products of dimethylaminoethyl methacrylate with at least one sulfate chosen from dimethyl sulfate and diethyl sulfate.

9. The roll-on applicator according to claim 3, wherein said at least one component is chosen from amphoteric fixing polymers resulting from the copolymerization of (i) a monomer derived from a vinyl compound substituted with at least one carboxylic group and (ii) a basic monomer derived from a substituted vinyl compound comprising at least one basic atom.

10. The roll-on applicator according to claim 3, wherein said at least one component is chosen from amphoteric fixing polymers chosen from partially and completely crosslinked and alkylated polyamino amides partially derived from polyamino amides of formula:

   (II)

wherein:
   $R_{10}$ is a divalent group derived from compounds chosen from: saturated dicarboxylic acids, dicarboxylic aromatic acids, carboxylic aliphatic acids chosen from monocarboxylic aliphatic acids and dicarboxylic aliphatic acids comprising at least one ethylenic double bond, and esters of ($C_1$–$C_6$)alkanols of said acids, and $R_{10}$ is also a divalent group derived from the addition of any one of the aforementioned acids with an amine chosen from bis(primary) and bis(secondary) amines, and Z is a divalent group derived from polyalkylene-polyamines chosen from bis(primary), mono- and bis(secondary) polyalkylene-polyamines.

11. The roll-on applicator according to claim 3, wherein said at least one component is chosen from amphoteric fixing polymers comprising at least one zwitterionic unit of formula:

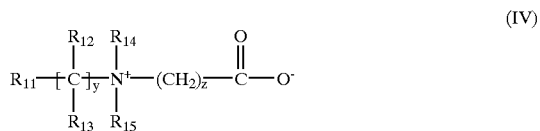   (IV)

wherein:
   $R_{11}$ is chosen from the residues of polymerizable unsaturated groups,
   y and z, which may be identical or different, are each chosen from integers ranging from 1 to 3,
   $R_{12}$ and $R_{13}$, which may be identical or different, are each chosen from hydrogen atoms and methyl, ethyl, and propyl groups,
   $R_{14}$ and $R_{15}$, which may be identical or different, are each chosen from hydrogen atoms and alkyl groups, provided that the sum of the carbon atoms in $R_{14}$ and $R_{15}$ does not exceed 10.

12. The roll-on applicator according to claim 11, wherein $R_{11}$ is chosen from the residues of acrylates, methacrylates, acrylamides, and methacrylamides.

13. The roll-on applicator according to claim 3, wherein said at least one component is chosen from amphoteric fixing polymers derived from chitosan comprising at least one monomeric unit chosen from the following formulae:

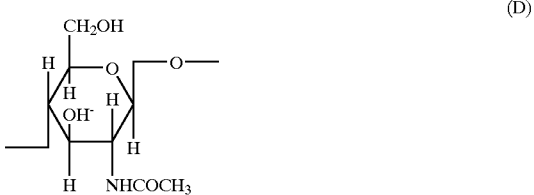   (D)

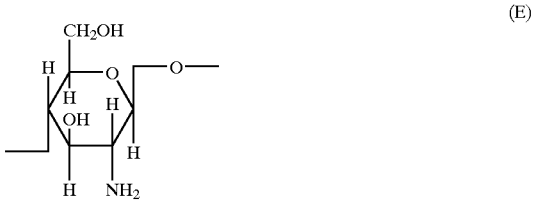   (E)

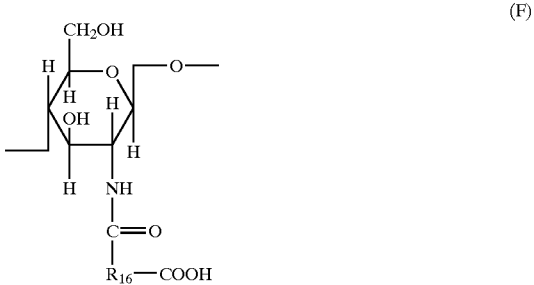   (F)

wherein the unit (D) is present in an amount ranging from 0% to 30%, by weight relative to the total weight of said polymer, the unit (E) is present in an amount ranging from 5% to 50%, by weight relative to the total weight of said polymer, and the unit (F) is present in an amount ranging from 30% to 90%, by weight relative to the total weight of said polymer, and wherein in said unit (F), $R_{16}$ chosen from groups of formula:

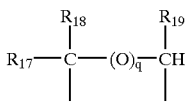

wherein:
q is equal to 0 or 1, and
(i) when q is equal to 0, $R_{17}$, $R_{18}$ and $R_{19}$, which may be identical or different, are each chosen from hydrogen, methyl groups, hydroxyl groups, acetoxy groups, amino groups, monoalkylamine groups, dialkylamine groups, and alkylthio groups, provided that at least one of the $R_{17}$, $R_{18}$ and $R_{19}$ groups is hydrogen;
when monoalkylamine and dialkylamine groups are used they may be optionally interrupted by at least one nitrogen atom and optionally substituted with at least one group chosen from amine, hydroxyl, carboxyl, alkylthio, and sulfonic groups;
when alkylthio groups are used, the alkyl portion of said alkylthio group carries an amino group; and
(ii) when q is equal to 1, $R_{17}$, $R_{18}$ and $R_{19}$ are each chosen from hydrogen.

14. The roll-on applicator according to claim 3, wherein said at least one component is chosen from amphoteric fixing polymers derived from the N-carboxyalkylation of chitosan.

15. The roll-on applicator according to claim 3, wherein said at least one component is chosen from amphoteric fixing polymers of the formula (VI):

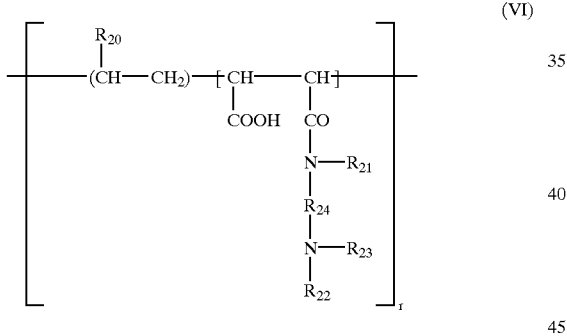

wherein:
r is chosen such that the number average molecular weight of said polymer ranges from 500 to 6,000,000;
$R_{20}$ is chosen from hydrogen atoms and $CH_3O$, $CH_3CH_2O$ and phenyl groups and higher homologues of said $CH_3O$ and $CH_3CH_2O$ groups, said higher homologues comprising up to 6 carbon atoms;
$R_{21}$ is chosen from hydrogen atoms and lower alkyl groups;
$R_{22}$ is chosen from hydrogen atoms and lower alkyl groups;
$R_{23}$ is chosen from lower alkyl groups and groups of the formula: —$R_{24}$—$N(R_{22})_2$, wherein $R_{24}$ is chosen from —$CH_2$—$CH_2$—, —$CH_2$—$CH_2$—$CH_2$— and —$CH_2$—$CH(CH_3)$— groups and higher homologues of said —$CH_2$—$CH_2$—, —$CH_2$—$CH_2$—$CH_2$— and —$CH_2$—$CH(CH_3)$— groups, said higher homologues comprising up to 6 carbon atoms, and wherein $R_{22}$ is defined above,
wherein said lower alkyl groups contain from 1 to 6 carbon atoms.

16. The roll-on applicator according to claim 3, wherein said at least one component is chosen from —D—X—D—X amphoteric fixing polymers chosen from:
a) polymers derived from the reaction of at least one compound chosen from chloroacetic acid and sodium chloroacetate with at least one compound comprising at least one unit of formula (XVII):

   (VII)

wherein D is a group:

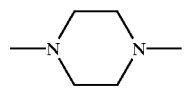

and X is chosen from the symbols E and E', which may be identical or different, wherein E and E' are each chosen from bivalent groups chosen from alkylene groups comprising at least one chain chosen from linear and branched chains comprising up to 7 carbon atoms in the principal chain, and wherein said at least one chain may be optionally substituted with at least one hydroxyl group and may comprise 1 to 3 rings chosen from aromatic and non-aromatic, heterocyclic rings, and may optionally comprise at least one atom chosen from oxygen, nitrogen, and sulfur atoms; wherein:
the at least one optional atom is present in the form of at least one group chosen from ether, thioether, sulfoxide, sulfone, sulfonium, alkylamine, alkenylamine, hydroxyl, benzylamine, amine oxide, quaternary ammonium, amide, imide, alcohol, ester, and urethane groups; and
b) polymers of formula:

   (VII')

wherein D is:

and X is chosen from the symbols E and E' and wherein at least one X is chosen from E' wherein:
E is chosen from bivalent groups chosen from alkylene groups comprising at least one chain chosen from linear and branched chains comprising up to 7 carbon atoms in the principal chain, and wherein said at least one chain may be optionally substituted with at least one hydroxyl group and may comprise 1 to 3 rings chosen from aromatic and nonaromatic, heterocyclic rings, and may optionally comprise at least one atom chosen from oxygen, nitrogen, and sulfur atoms;
wherein:
the at least one optional atom is present in the form of at least one group chosen from ether, thioether, sulfoxide, sulfone, sulfonium, alkylamine, alkenylamine, hydroxyl, benzylamine, amine oxide, quaternary ammonium, amide, imide, alcohol, ester, and urethane groups, and
E' is a bivalent group chosen from alkylene groups comprising at least one chain chosen from linear and branched chains comprising up to 7 carbon atoms in the principal chain, wherein said at least one chain is optionally substituted with at least one hydroxyl group and wherein said at least one chain comprises at least one nitrogen atom substituted with an alkyl chain, wherein said alkyl chain is optionally interrupted by an oxygen atom and, wherein said alkyl chain comprises at least one functional group chosen from carboxyl and hydroxyl functional groups, and wherein said at least one alkyl chain is betainized by reaction with a reactant chosen from chloroacetic acid and sodium chloroacetate.

17. The roll-on applicator according to claim 3, wherein said at least one component is chosen from amphoteric fixing polymers chosen from ($C_1$–$C_5$)alkyl vinyl ether/maleic anhydride copolymers partially modified by semiamidation with an N,N-dialkylaminoalkylamine.

18. The roll-on applicator according to claim 3, wherein said at least one component is chosen from nonionic fixing polymers chosen from:

polyalkyloxazolines;

vinyl acetate homopolymers;

copolymers of vinyl acetate and of acrylic ester;

copolymers of vinyl acetate and of ethylene;

copolymers of vinyl acetate and of maleic ester;

copolymers of polyethylene and of maleic anhydride;

alkyl acrylate homopolymers and alkyl methacrylate homopolymers;

acrylic ester copolymers;

copolymers of acrylonitrile and of a nonionic monomer;

copolymers of alkyl acrylate and of urethane;

polyamides; and guar gums selected from chemically modified nonionic guar gums and chemically unmodified nonionic guar gums.

19. The roll-on applicator according to claim 18, wherein the acrylic ester copolymers are selected from copolymers of alkyl acrylates and of alkyl methacrylates.

20. The roll-on applicator according to claim 18, wherein said nonionic monomer is chosen from butadiene and alkyl (meth)acrylates.

21. The roll-on applicator according to claim 3, wherein said at least one component is chosen from polyurethane fixing polymers chosen from functionalized polyurethanes and nonfunctionalized polyurethanes, wherein said polyurethane fixing polymers may optionally comprise at least one silicone.

22. The roll-on applicator according to claim 3, wherein said at least one component is chosen from grafted silicone fixing polymers comprising a polysiloxane portion and a portion comprising a non-silicone organic chain, one of the two portions comprising the main chain of the polymer and the other being grafted onto the main chain.

23. The roll-on applicator according to claim 22, wherein said grafted silicone fixing polymers are chosen from copolymers obtained by radical polymerization of a monomer composition comprising:

a) from 50% to 90% by weight of tert-butyl acrylate;

b) from 0% to 40% by weight of acrylic acid; and c) from 5% to 40% by weight of silicone macromer of formula:

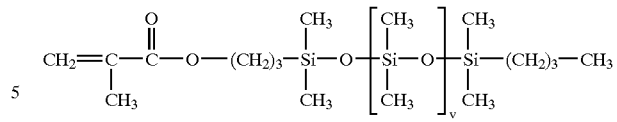

wherein v is a number ranging from 5 to 700, the weight percentages being relative to the total weight of the monomers.

24. The roll-on applicator according to claim 2, wherein the at least one component is chosen from at least one beneficial agent.

25. The roll-on applicator according to claim 24, wherein the at least one beneficial agent is chosen from synthetic oils, mineral oils, vegetable oils, fluorinated oils, perfluorinated oils, natural waxes, synthetic waxes, silicones, cationic polymers, ceramide compounds, cationic surfactants, fatty amines, fatty acids, fatty acid derivatives, fatty alcohols, and fatty alcohol derivatives.

26. The roll-on applicator according to claim 25, wherein the synthetic oils are chosen from hydrogenated polybutene polyolefins, nonhydrogenated polybutene polyolefins, hydrogenated polydecene polyolefins, and nonhydrogenated polydecene polyolefins.

27. The roll-on applicator according to claim 25, wherein the mineral oils are chosen from the group formed by hydrocarbons.

28. The roll-on applicator according to claim 27, wherein the hydrocarbons are selected from hexadecane and liquid paraffin.

29. The roll-on applicator according to claim 25, wherein the vegetable oils are selected from sunflower oils, maize oils, soybean oils, avocado oils, jojoba oils, cucumber oils, grape seed oils, sesame seed oils, and hazelnut oils.

30. The roll-on applicator according to claim 25, wherein the natural and synthetic waxes are selected from carnauba wax, candelilla wax, esparto wax, paraffin wax, ozokerite, vegetable waxes, and animal waxes.

31. The roll-on applicator according to claim 30, wherein the vegetable waxes are selected from olive tree wax, rice wax, hydrogenated jojoba wax and absolute flower waxes.

32. The roll-on applicator according to claim 30, wherein the animal waxes are selected from beeswaxes and modified beeswaxes.

33. The roll-on applicator according to claim 25, wherein the cationic polymers are chosen from polymers which comprise at least one unit comprising at least one group chosen from primary amine groups, secondary amine groups, tertiary amine groups, and quaternary amine groups, wherein said at least one group forms part of the polymer skeleton, or is carried by at least one substituent directly connected to said polymer skeleton.

34. The roll-on applicator according to claim 25, wherein the cationic polymers are chosen from quaternary cellulose ether derivatives, cationic cyclopolymers, cationic polysaccharides, quaternary polymers of vinylpyrrolidone, and quaternary polymers of vinylimidazole.

35. The roll-on applicator according to claim 34, wherein the cationic cyclopolymers are chosen from diallyldimethylammonium chloride homopolymers, and copolymers of diallyidimethylammonium chloride and of acrylamide.

36. The roll-on applicator according to claim 34, wherein the quaternary cellulose ether derivatives are chosen from hydroxyethylcelluloses which have reacted with an epoxide substituted with a trimethylammonium group.

37. The roll-on applicator according to claim 34, wherein the cationic polysaccharides are chosen from guar gums modified with at least one 2,3-epoxypropyl-trimethylammonium salt.

38. The roll-on applicator according to claim 25, wherein said cationic polymers are chosen from homo- and co-polymers derived from at least one monomer chosen from acrylic esters, methacrylic esters and amides, wherein said homo- and co-polymers comprise at least one unit chosen from units of formulae:

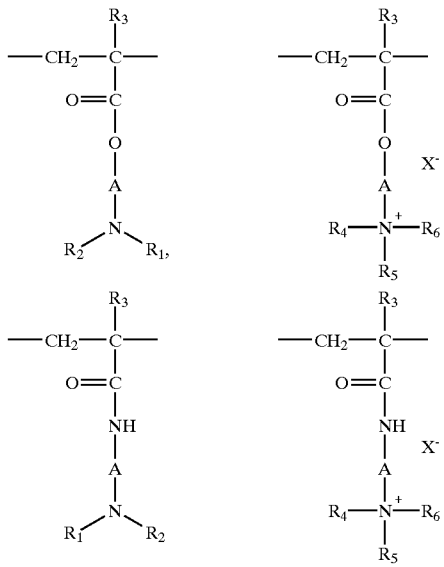

wherein:
- $R_3$, which may be identical or different, are each chosen from hydrogen atoms and $CH_3$ groups;
- —A, which may be identical or different, are each chosen from linear and branched alkyl groups comprising from 1 to 6 carbon atoms and hydroxyalkyl groups comprising from 1 to 4 carbon atoms;
- $R_4$, $R_5$ and $R_6$, which may be identical or different, are each chosen from alkyl groups comprising from 1 to 18 carbon atoms and benzyl groups;
- $R_1$ and $R_2$, which may be identical or different, are each chosen from a hydrogen atom and alkyl groups comprising from 1 to 6 carbon atoms; and
- $X^-$ is an anion chosen from anions derived from at least one inorganic acid and anions derived from at least one organic acid.

39. The roll-on applicator according to claim 25, wherein said cationic polymers are chosen from quaternary cellulose ether derivatives, cationic cellulose derivatives, cationic polysaccharides, cyclopolymers of alkyldiallylamine, cyclopolymers of dialkyldiallylammonium, quaternary polymers of vinylpyrrolidone, quaternary polymers of vinylimidazole, and crosslinked (meth)acryloyloxy($C_1$–$C_4$)alkyltri($C_1$–$C_4$)alkylammonium salt polymers.

40. The roll-on applicator according to claim 25, wherein said cationic polymers comprise (A) (i) at least one piperazinyl unit and (ii) at least one group chosen from divalent alkylene groups and divalent hydroxyalkylene groups, wherein said at least one group optionally comprises at least one chain chosen from straight chains and branched chains, wherein said at least one chain is optionally interrupted by at least one entity chosen from oxygen atoms, sulfur atoms, nitrogen atoms, aromatic rings, and heterocyclic rings, (B) the oxidation products of said cationic polymers, and (C) the quaternization products of said cationic polymers.

41. The roll-on applicator according to claim 25, wherein said cationic polymers chosen from water-soluble polyamino amides prepared via at least one polycondensation reaction of at least one acidic compound and at least one polyamine compound, wherein said polyamino amides may be crosslinked with at least one crosslinking agent chosen from epihalohydrins, diepoxides, dianhydrides, unsaturated dianhydrides, bis-unsaturated derivatives, bis-halohydrins, bis-azetidiniums, bis-haloacyidiamines, bis-alkyl,halides, and oligomers derived from reaction of at least one difunctional compound with at least one compound chosen from bis-halohydrins, bis-azetidiniums, bis-haloacyldiamines, bis-alkyl halides, epihalohydrins, diepoxides and bis-unsaturated derivatives, wherein said crosslinking agent is used in a proportion ranging from 0.025 mol to 0.35 mol per amine group of said polyamino amide, wherein said polyamino amides may optionally be alkylated, and wherein if said polyamino amides comprise at least one tertiary amine group, said polyamino amides may optionally be quaternized.

42. The roll-on applicator according to claim 25, wherein said cationic polymers are chosen from polyamino amide derivatives derived from condensation of at least one polyalkylene polyamine with at least one polycarboxylic acid, followed by alkylation with at least one difunctional agent.

43. The roll-on applicator according to claim 25, wherein said cationic polymers are chosen from polymers derived from reaction of (i) at least one polyalkylene polyamine comprising two primary amine groups and at least one secondary amine group with (ii) at least one dicarboxylic acid chosen from diglycolic acid and saturated aliphatic dicarboxylic acids comprising from 3 to 8 carbon atoms.

44. The roll-on applicator according to claim 25, wherein said cationic polymers are chosen from homopolymers and copolymers comprising, as the main constituent of the chain, at least one unit chosen from units of formulae (VI) and (VI'):

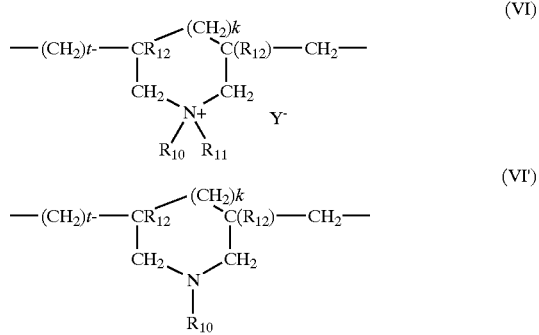

wherein:
- k and t, which may be identical or different, are each chosen from 0 and 1, with the proviso that the sum of k+t is equal to 1;
- $R_{12}$, which may be identical or different, are each chosen from a hydrogen atom and a methyl group;
- $R_{10}$ and $R_{11}$, which may be identical or different, are each chosen from alkyl groups comprising from 1 to 22 carbon atoms, hydroxyalkyl groups wherein the alkyl portion of said hydroxyalkyl group optionally comprises from 1 to 5 carbon atoms, lower $C_1$–$C_4$ amidoalkyl groups, and, in addition,
- $R_{10}$ and $R_{11}$, together with the nitrogen cation to which they are commonly attached, form at least one cationic heterocyclic group; and
- $Y^-$ is an anion.

45. The roll-on applicator according to claim 25, wherein said cationic polymers are chosen from quaternary diammonium polymers comprising at least two repeating units of formula:

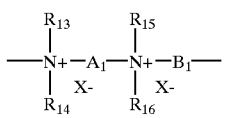
(VII)

wherein:
- $R_{13}$, $R_{14}$, $R_{15}$ and $R_{16}$, which may be identical or different, can each be chosen from aliphatic groups comprising from 1 to 20 carbon atoms, alicyclic groups comprising from 3 to 20 carbon atoms, arylaliphatic groups comprising from 4 to 20 carbon atoms, and lower hydroxyalkylaliphatic groups, and in addition,
- $R_{13}$, $R_{14}$, $R_{15}$ and $R_{16}$, separately or at least two of which together, with the nitrogen cations to which they are attached, can form at least one cationic heterocycle optionally comprising an additional heteroatom other than nitrogen, and in addition,
- $R_{13}$, $R_{14}$, $R_{15}$ and $R_{16}$, which may be identical or different, can each be chosen from linear and branched $C_1$–$C_6$ alkyl groups substituted with at least one group chosen from nitrile groups, ester groups, acyl groups, amide groups and groups chosen from groups of formulae —CO—O—$R_{17}$—D and —CO—NH—$R_{17}$—D, wherein $R_{17}$ is chosen from alkylene groups and D is chosen from quaternary ammonium groups;
- $A_1$ and $B_1$, which may be identical or different, are each chosen from polymethylene groups comprising from 2 to 20 carbon atoms chosen from linear and branched, saturated and unsaturated polymethylene groups wherein said polymethylene groups may optionally comprise, optionally linked to and optionally intercalated in the main chain, at least one entity chosen from aromatic rings, oxygen atoms, sulfur atoms, sulfoxide groups, sulfone groups, disulfide groups, amino groups, alkylamino groups, hydroxyl groups, quaternary ammonium groups, ureido groups, amide groups and ester groups; and
- $X^-$ is an anion chosen from anions derived from inorganic acids and anions derived from organic acids; and
- $A_1$, $R_{13}$ and $R_{15}$ may optionally form, together with the two quaternized nitrogen atoms to which they are attached, at least one quaternized piperazine ring;
- with the proviso that if $A_1$ is chosen from linear and branched, saturated and unsaturated polymethylene groups and linear and branched, saturated and unsaturated hydroxypolymethylene groups, $B_1$ may also be chosen from groups of formula:

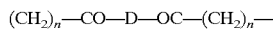

wherein D is chosen from:
  a) glycol residues of formula: —O—Z—O—, wherein Z is chosen from linear and branched hydrocarbon groups and groups chosen from groups of formulae:

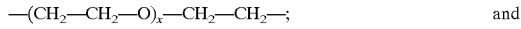 and

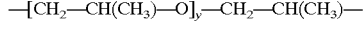

wherein x and y, which may be identical or different, are each chosen from integers ranging from 1 to 4 (in which case x and y represent a defined and unique degree of polymerization) and any number ranging from 1 to 4 (in which case x and y represent an average degree of polymerization);
  b) bis-secondary diamine residues;
  c) bis-primary diamine residues chosen from residues of formula: —NH—Y—NH—, wherein Y is chosen from linear and branched hydrocarbon groups and residues of formula

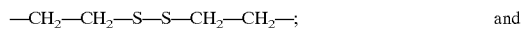 and d) ureylene groups of formula: —NH—CO—NH— wherein n in the above formula ranges from 1 to 6.

46. The roll-on applicator according to claim 25, wherein said cationic polymers are chosen from polyquaternary ammonium polymers comprising units of formula (VIII):

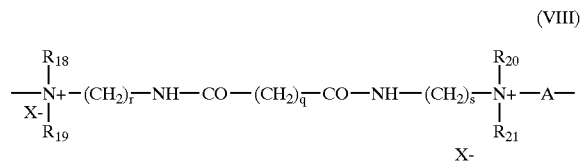
(VIII)

wherein:
- $R_{18}$, $R_{19}$, $R_{20}$ and $R_{21}$, which may be identical or different, are each chosen from a hydrogen atom, a methyl group, an ethyl group, a propyl group, a β-hydroxyethyl group, a β-hydroxypropyl group and —$CH_2CH_2(OCH_2CH_2)_p$OH groups wherein p is an integer ranging from 0 to 6, with the proviso that $R_{18}$, $R_{19}$, $R_{20}$ and $R_{21}$ are all not simultaneously chosen from a hydrogen atom;
- r and s, which may be identical or different, are each chosen from integers ranging from 1 to 6;
- q is an integer ranging from 1 to 34;
- $X^-$ is an anion; and
- A is chosen from dihalide groups and groups of formula 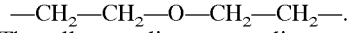.

47. The roll-on applicator according to claim 25, wherein said cationic polymers are chosen from cationic proteins, cationic protein hydrolysates, polyalkyleneimines, polymers comprising at least one vinylpyridine unit, polymers comprising at least one vinylpyridinium unit, condensates of polyamines, condensates of epichlorohydrin, quaternary polyureylenes, and chitin derivatives.

48. The roll-on applicator according to claim 25, wherein said silicones are chosen from polyorganosiloxanes that are insoluble in the composition.

49. The roll-on applicator according to claim 25, wherein said silicones are chosen from non-volatile silicones chosen from polyalkylsiloxanes, polyarylsiloxanes, polyalkylarylsiloxanes, silicone gums, silicone resins, and polyorganosiloxanes modified with at least one organofunctional group.

50. The roll-on applicator according to claim 49, wherein said silicones are chosen from polyalkylsiloxanes.

51. The roll-on applicator according to claim 25, wherein said silicones are chosen from nonvolatile polyorganosiloxanes chosen from polyalkylsiloxanes comprising trimethylsilyl end groups and polysiloxanes comprising at least one amine group.

52. The roll-on applicator according to claim 25, wherein said ceramide compounds are chosen from:
  2-(N-linoleoylamino)octadecane-1,3-diol,
  2-(N-oleoylamino)octadecane-1,3-diol, 2-(N-palmitoylamino)octadecane-1,3-diol,
2-(N-stearoylamino)octadecane-1,3-diol,
2-(N-behenoylamino)octadecane-1,3-diol,
2-[N-(2-hydroxypalmitoyl)amino]octadecane-1,3-diol,
2-(N-stearoylamino)octadecane-1,3,4-triol and stearoylphytosphingosine,
2-(N-palmitoylamino)hexadecane-1,3-diol,
bis(N-hydroxyethyl-N-cetyl)malonamide,
the N-(2-hydroxyethyl)-N-(3-cetyloxy-2-hydroxypropyl) amide of cetylic acid, and
N-docosanoyl-N-methyl-D-glucamine.

53. The roll-on applicator according to claim 25, wherein said cationic surfactants are chosen from salts of optionally polyoxyalkylenated primary fatty amines, salts of optionally polyoxyalkylenated secondary fatty amines, salts of optionally polyoxyalkylenated tertiary fatty amines, quaternary ammonium salts, imidazoline derivatives, and amine oxides with a cationic nature.

54. The roll-on applicator according to claim 25, wherien said cationic surfactants are chosen from quaternary ammonium salts chosen from:

quaternary ammonium salts of formula (IV) below:

in which:
the radicals $R_1$, $R_2$, $R_3$, and $R_4$, which may be identical or different, are independently chosen from linear and branched aliphatic radicals comprising from 1 to 30 carbon atoms, and aromatic radicals, wherein the aliphatic radicals optionally comprise at least one atom chosen from hetero atoms and halogen atoms, and
$X^-$ is an anion chosen from the group of halides, phosphates, anions derived from organic acids, ($C_2$–$C_6$)alkyl sulfates, alkyl sulfonates, and alkylaryl sulfonates;

quaternary ammonium salts of imidazolinium of formula (V) below:

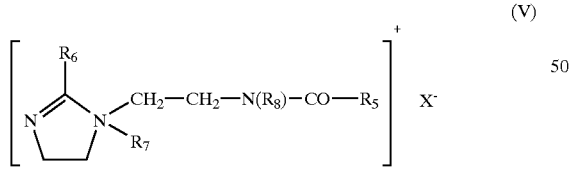

in which:
$R_5$ is chosen from alkenyl and alkyl radicals comprising from 8 to 30 carbon atoms,
$R_6$ is chosen from a hydrogen atom, $C_1$–$C_4$ alkyl radicals, and alkenyl and alkyl radicals comprising from 8 to 30 carbon atoms,
$R_7$ is chosen from $C_1$–$C_4$ alkyl radicals,
$R_8$ is chosen from a hydrogen atom and $C_1$–$C_4$ alkyl radicals, and
$X^-$ is an anion chosen from halides, phosphates, acetates, lactates, alkyl sulfates, alkyl sulfonates, and alkylaryl sulfonates;

diquaternary ammonium salts of formula (VI):

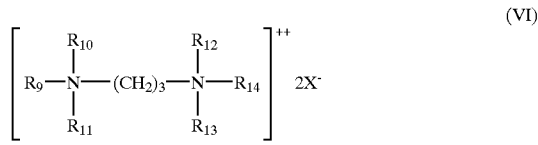

in which:
$R_9$ is chosen from aliphatic radicals comprising from 16 to 30 carbon atoms,
$R_{10}$, $R_{11}$, $R_{12}$, $R_{13}$ and $R_{14}$, which may be identical or different, are independently chosen from a hydrogen atom and alkyl radicals comprising from 1 to 4 carbon atoms, and
$X^-$ is an anion chosen from halides, acetates, phosphates, nitrates and methyl sulfates;

quaternary ammonium salts of formula (VII) below comprising at least one ester function:

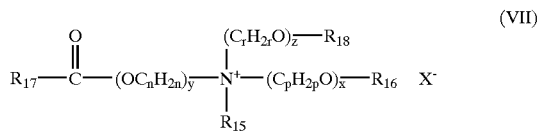

in which:
$R_{15}$ is chosen from $C_1$–$C_6$ alkyl radicals and $C_1$–$C_6$ hydroxyalkyl and $C_1$–$C_6$ dihydroxyalkyl radicals;
$R_{16}$ is chosen from:
acyl groups of the following formula:

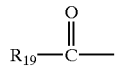

wherein $R_{19}$ is defined below,
linear and branched, saturated and unsaturated, $C_1$–$C_{22}$ hydrocarbon-based radicals, and
a hydrogen atom;
$R_{18}$ is chosen from:
acyl groups of the following formula:

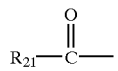

wherein $R_{21}$, is defined below,
linear and branched, saturated and unsaturated, $C_1$–$C_6$ hydrocarbon-based radicals, and
a hydrogen atom;
$R_{17}$, $R_{19}$ and $R_{21}$, which may be identical or different, are independently chosen from linear and branched, saturated and unsaturated, $C_7$–$C_{21}$ hydrocarbon-based radicals;
n, p and r, which may be identical or different, are independently integers ranging from 2 to 6;
y is an integer ranging from 1 to 10;
x and z, which may be identical or different, are independently integers ranging from 0 to 10; and
$X^-$ is chosen from simple and complex, organic and inorganic anions; and
provided that the sum x+y+z is from 1 to 15, and that when x is 0, then $R_{16}$ is chosen from linear and branched, saturated and unsaturated, $C_1$–$C_{22}$ hydrocarbon-based radicals, and that when z is 0, then $R_{18}$ is chosen from linear and branched, saturated and unsaturated, $C_1$–$C_6$ hydrocarbon-based radicals.

55. The roll-on applicator according to claim 54, wherein in said quaternary ammonium salts of formula (VII):
$R_{15}$ is chosen from methyl and ethyl radicals,
x and y are equal to 1;
z is equal to 0 or 1;
n, p and r are equal to 2;
$R_{16}$ is chosen from:

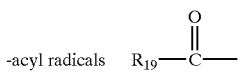

wherein $R_{19}$ is defined below,
methyl, ethyl and $C_{14}$–$C_{22}$ hydrocarbon-based radicals, and a hydrogen atom;
$R_{18}$ is chosen from:

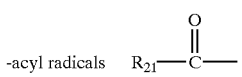

wherein $R_{21}$ is defined below,
a hydrogen atom; and
$R_{17}$, $R_{19}$ and $R_{21}$, which may be identical or different, are independently chosen from linear and branched, saturated and unsaturated, $C_{13}$–$C_{17}$ hydrocarbon-based radicals.

56. The roll-on applicator according to claim 55, wherein $R_{17}$, $R_{19}$ and $R_{21}$ are chosen from linear and branched, saturated and unsaturated $C_{13}$–$C_{17}$ aliphatic radicals.

57. The roll-on applicator according to claim 55, wherein the hydrocarbon-based radicals are chosen from linear hydrocarbon-based radicals.

58. The roll-on applicator according to claim 54, wherein the compounds of formula (VII) are chosen from diacyloxyethyldimethylammonium, diacyloxyethylhydroxyethylmethylammonium, monoacyloxyethyldihydroxyethylmethylammonium, triacyloxyethylmethylammonium and monoacyloxyethylhydroxyethyldimethylammonium salts.

59. The roll-on applicator according to claim 58, wherein said monoacyloxyethylhydroxyethyldimethylammonium salts are chosen from monoacyloxyethylhydroxyethyldimethylammonium chloride salts and monoacyloxyethylhydroxyethyldimethylammonium methyl sulfate salts.

60. The roll-on applicator according to claim 55, wherein when $R_{16}$ and $R_{18}$ are chosen from acyl radicals, said acyl radicals are obtained from plant oils chosen from palm oil and sunflower oil.

61. The roll-on applicator according to claim 54, wherein $X^-$ of said quaternary ammonium salts of formula (IV) is an anion chosen from chloride, bromide, iodide, methyl sulfate, acetate, and lactate.

62. The roll-on applicator according to claim 54, wherein said aromatic radicals of said quaternary ammonium salts of formula (IV) are chosen from aryl and alkylaryl.

63. The roll-on applicator according to claim 54, wherein said hetero atoms of said quaternary ammonium salts of formula (IV) are chosen from oxygen, nitrogen, and sulfur.

64. The roll-on applicator according to claim 54, wherein said $R_5$ of formula (V) is chosen from radicals derived from tallow fatty acid.

65. The roll-on applicator according to claim 54, wherein in said quaternary ammonium salts of imidazolinium of formula (V):
$R_5$ and $R_6$, which may be identical or different, are independently chosen from alkenyl and alkyl radicals comprising from 12 to 21 carbon atoms,
$R_7$ is methyl, and
$R_8$ is hydrogen.

66. The roll-on applicator according to claim 65, wherein said $R_5$ and $R_6$, which may be identical or different, are independently chosen from radicals derived from tallow fatty acid.

67. The roll-on applicator according to claim 4, wherein said diquaternary ammonium salts comprise propane tallow diammonium dichloride.

68. The roll-on applicator according to claim 54, wherein said $R_{15}$ alkyl radicals of said quaternary ammonium salts of formula (VII) are chosen from linear and branched $C_1$–$C_6$ alkyl radicals.

69. The roll-on applicator according to claim 54, wherein said $R_{15}$ radicals are linear radicals.

70. The roll-on applicator according to claim 69, wherein said $R_{15}$ radicals are chosen from methyl, ethyl, hydroxyethyl, and dihydroxypropyl.

71. The roll-on applicator according to claim 54, wherein said sum of x+y +z of said quaternary ammonium salts of formula (VII) ranges from 1 to 10.

72. The roll-on applicator according to claim 25, wherein said fatty alcohols are chosen from lauryl alcohol, myristyl alcohol, cetyl alcohol, stearyl alcohol, oleyl alcohol, isostearyl alcohol, isocetyl alcohol, oleyl alcohol, and lauryl alcohols oxyethylenated with 2 to 8 mol of ethylene oxide.

73. The roll-on applicator according to claim 25, wherein said fatty acids are chosen from myristic acid, palmitic acid, stearic acid, behenic acid, oleic acid, linoleic acid, linolenic acid, and isostearic acid.

74. The roll-on applicator according to claim 3, wherein said at least one component chosen from anionic, amphoteric, and nonionic fixing polymers is present in an amount ranging from 0.1% to 10% by weight, relative to the total weight of the final composition.

75. The roll-on applicator according to claim 74, wherein said at least one component chosen from anionic, amphoteric, and nonionic fixing polymers is present in an amount ranging from 0.5% to 5% by weight, relative to the total weight of the final composition.

76. The roll-on applicator according to claim 24, wherein said at least one beneficial agent is present in an amount ranging from 0.01% to 15% by weight, relative to the total weight of the final composition.

77. The roll-on applicator according to claim 76, wherein said at least one beneficial agent is present in an amount ranging from 0.05% to 10% by weight, relative to the total weight of the final composition.

78. The roll-on applicator according to claim 1, further comprising at least one thickening agent chosen from natural thickening agents and synthetic thickening agents.

79. The roll-on applicator according to claim 78, wherein the natural thickening agents are chosen from xanthan gum, scleroglucan gum, gellan gum, rhamsan gum, alginates, maltodextrin, starch, derivatives of starch, karaya gum, locus bean flour, guar gums, celluloses, and derivatives of celluloses.

80. The roll-on applicator according to claim 78, wherein the synthetic thickening agents are chosen from polymers of acrylic acid, polymers of methacrylic acid, and copolymers of acrylic acid and methacrylic acid.

81. The roll-on applicator according to claim 78, wherein the synthetic thickening agents are chosen from:
- crosslinked homopolymers of 2-acrylamido-2-methylpropanesulfonic acid;
- optionally crosslinked copolymers of acrylamide and of ammonium acrylate;
- optionally crosslinked copolymers of acrylamide, methacrylamide, and methacryloyloxyethyltrimethylammonium chloride; and
- partially and completely neutralized and optionally crosslinked copolymers of acrylamide and of 2-acrylamido-2-methylpropanesulfonic acid.

82. The roll-on applicator according to claim 1, wherein said hair dyes are chosen from inorganic and organic pigments; soluble direct dyes belonging to the following classes: nitro, azo, quinone, xanthene, triarylmethane and indoamine; and oxidation dyes.

83. The roll-on applicator according to claim 1, further comprising at least one additive chosen from anionic surfactants, nonionic surfactants, amphoteric surfactants, polyols, pigments, dyes, fragrances, screening agents, preservatives, proteins, vitamins, provitamins, and polymers.

84. The roll-on applicator according to claim 83, wherein said polyols are chosen from glycol and glycerol.

85. A cosmetic process comprising applying to the hair at least one component chosen from anionic, amphoteric and nonionic fixing polymers; beneficial agents; and hair dyes; wherein said at least one component is applied to the hair by use of a roll-on applicator comprising a container and a rotatable application member on the container, the container containing a hair composition devoid of carboxylic surfactant, said hair composition comprising, in a cosmetically acceptable medium, at least one component chosen from:
  (i) anionic, amphoteric, and nonionic fixing polymers;
  (ii) beneficial agents; and
  (iii) hair dyes;
  wherein the roll-on applicator is capable of directly depositing on the hair said at least one component.

86. A roll-on applicator comprising a container and a rotatable application member on the container, the container containing a hair composition devoid of carboxylic surfactant, said hair composition comprising, in a cosmetically acceptable medium, at least one component chosen from:
  (i) beneficial agents; and
  (ii) hair dyes;
  wherein the roll-on applicator is capable of directly depositing on the hair said at least one component.

* * * * *

UNITED STATES PATENT AND TRADEMARK OFFICE
CERTIFICATE OF CORRECTION

PATENT NO. : 6,635,262 B2
DATED : October 21, 2003
INVENTOR(S) : Hervé Jourdan et al.

It is certified that error appears in the above-identified patent and that said Letters Patent is hereby corrected as shown below:

Column 44,
Line 67, "$R_{16}$ chosen" should read -- $R_{16}$ is chosen --.

Column 48,
Line 61, "diallyidimethylammonium" should read -- diallyldimethylammonium --.

Column 50,
Line 7, "bis-haloacyidiamines, bis-alkyl,halides," should read
-- bis-haloacyldiamines, bis-alkyl halides, --.

Column 53,
Line 21, "wherien" should read -- wherein --.

Column 54,
Line 50, "$R_{21}$, is" should read -- $R_{21}$ is --.

Column 56,
Line 13, "claim 4," should read -- claim 54, --.

Signed and Sealed this

Second Day of March, 2004

JON W. DUDAS
*Acting Director of the United States Patent and Trademark Office*